(12) United States Patent
Chang et al.

(10) Patent No.: US 8,288,348 B2
(45) Date of Patent: *Oct. 16, 2012

(54) CYCLOSPORIN COMPOSITIONS

(75) Inventors: James N. Chang, Newport Beach, CA (US); Orest Olejnik, Coto De Caza, CA (US); Bruce A. Firestone, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/917,448

(22) PCT Filed: Jul. 12, 2006

(86) PCT No.: PCT/US2006/026881
§ 371 (c)(1),
(2), (4) Date: Dec. 13, 2007

(87) PCT Pub. No.: WO2007/008894
PCT Pub. Date: Jan. 18, 2007

(65) Prior Publication Data
US 2008/0207494 A1 Aug. 28, 2008

(51) Int. Cl.
*A61K 38/12* (2006.01)
*A61P 35/00* (2006.01)

(52) U.S. Cl. ............................... 514/19.9
(58) Field of Classification Search .......... None
See application file for complete search history.

(56) References Cited

U.S. PATENT DOCUMENTS

| | | | | |
|---|---|---|---|---|
| 4,649,047 A * | 3/1987 | Kaswan | | 514/11 |
| 5,474,979 A * | 12/1995 | Ding et al. | | 514/11 |
| 5,981,607 A * | 11/1999 | Ding et al. | | 514/785 |
| 6,267,985 B1 * | 7/2001 | Chen et al. | | 424/451 |
| 6,555,526 B2 * | 4/2003 | Matsuo et al. | | 514/53 |
| 6,660,278 B1 * | 12/2003 | Larsson et al. | | 424/400 |
| 7,202,209 B2 * | 4/2007 | Chang et al. | | 514/9 |
| 7,276,476 B2 * | 10/2007 | Chang et al. | | 514/9 |
| 7,288,520 B2 * | 10/2007 | Chang et al. | | 514/9 |
| 7,297,679 B2 * | 11/2007 | Chang et al. | | 514/9 |
| 2003/0059470 A1 * | 3/2003 | Muller | | 424/489 |
| 2005/0074468 A1 * | 4/2005 | Kim et al. | | 424/400 |

FOREIGN PATENT DOCUMENTS

| | | |
|---|---|---|
| WO | WO02/09667 | 2/2002 |
| WO | WO03/053405 | 7/2003 |
| WO | WO2004/082625 | 9/2004 |
| WO | WO2005/032577 | 4/2005 |
| WO | WO2007/016073 | 2/2007 |

OTHER PUBLICATIONS http://www.csgnetwork.com/sgvisc.html (Specific gravity and viscosity of liquids, accessed online Apr. 27, 2009). 10 pages.*
http://www.jtbaker.com/msds/englishhtml/m7700.htm (Mineral oil, accesed online Apr. 27, 2009). 7 pages.*
Liebovitz et al. Our Experiences in Processing Maize (Corn) Germ Oil. JAOCS. 1983, vol. 60, No. 2, pp. 347A-351A.*
http://www.nutrition-partner.com/index.cfm?uuid=B3B76E7B2A5AE626678B8CA6435DACC6&frame=2&width=369&fscroll=1 (Lipofundin N 20%, accessed online Dec. 22, 2009), 2 pages.*
http://www.elmhurst.edu/~chm/vchembook/553phosglycerides.html (Phosphoglycerides or phospholipids, accessed online Dec. 22, 2009), 2 pages.*
Tamilvanan, et al., "The Potential of Lipid Emlsion for Ocular Delivery of Lipophilic Drugs," Europena Journal of Pharmaceutics, Elsevier Science, vol. 58, No. 2 (2004) pp. 357-368.
Database WPI Week 200044, Derwent Pub. Ltd., London, GB; An 2000-492678, XP002431884 & JP2000/143542, Abstract, year 2000, 2 pages.
Restasis® Package Insert, Restasis® (cyclosporine ophthalmic emulsion) 0.05%, Sterile, Preservative-Free, 2 pages, 2004, Allergan Inc. 2 pages.
Sandimmune® Package Insert, (cyclosporine oral solution), RxList, The Internet Drug Index, 3 pages, accessed online Jun. 22, 2006 at http://www.rxlist.com/cgi/generic3/cyclosporine.htm, 3 pages.

* cited by examiner

*Primary Examiner* — Marcela M Cordero Garcia
(74) *Attorney, Agent, or Firm* — Joel B. German; Debra D. Condino

(57) ABSTRACT

Cyclosporin A compositions are disclosed herein comprising an oil and a surfactant. These are useful in the treatment of dry eye disease.

3 Claims, No Drawings

CYCLOSPORIN COMPOSITIONS

RELATED APPLICATIONS

This is a national stage application under 35 U.S.C. 371 of PCT patent application PCT/US2006/026881, filed on Jul. 12, 2006, which claims the benefit of the following U.S. patent applications:
1. U.S. Ser. No. 11/181,509, filed Jul. 13, 2005
2. U.S. Ser. No. 11/181,187, filed Jul. 13, 2005, now U.S. Pat. No. 7,276,476
3. U.S. Ser. No. 11/181,409, filed Jul. 13, 2005;
4. U.S. Ser. No. 11/181,178, filed Jul. 13, 2005, now U.S. Pat. No. 7,297,679,
5. U.S. Ser. No. 11/181,428, filed Jul. 13, 2005, now U.S. Pat. No. 7,202,209

DESCRIPTION OF INVENTION

Disclosed herein is a composition comprising cyclosporin A, an oil, and a surfactant, wherein said composition is an ophthalmically acceptable emulsion, with the proviso that if the oil is castor oil the surfactant is not Polysorbate 80.

These compositions are useful for, among other things, the treatment of dry eye disease.

The Cyclosporin A

The cyclosporin A is preferably comprised in the composition in a concentration of from about 0.001% to about 0.4%.

Cyclosporin A is preferably comprised in an amount of from about 0.001% to about 0.1%; more preferably it is comprised in an amount of from about 0.005% to about 0.05%. Preferably, cyclosporin A is comprised in an amount of about 0.05%.

The Oil

The oil which is comprised may be selected from the following list 1:

List 1:
an oil having a specific gravity from 0.95 to 1.07: Anise oil, Castor oil, Clove oil, Cassia oil and Cinnamon oil;
an oil having a specific gravity from 0.90 to 0.95: Almond oil, Corn oil, Arachis oil, Cottonseed oil, Safflower oil, Maize oil, Linseed oil, Rapeseed oil, Soybean oil, Olive oil, Caraway oil, Rosemary oil, Peanut oil, Peppermint oil, Sunflower oil, Eucalyptus oil and Sesame oil; and
an oil having a specific gravity below 0.9, Mineral oil, Coriander oil, Lavender oil, Citronella oil, Juniper oil, Lemon oil, Orange oil, Clary sage oil, Nutmeg oil and Tea tree oil.

The Surfactant

Useful surfactants include, but are not limited to surfactants of the following classes:

Class A: Alcohols

These include but are not limited to those selected from the list A which is defined as follows:

List A $C_1$ to $C_{12}$ linear or branched monoalcohols;
glycerol oligomers or polymers, such as diglycerol;
  Diglycerol®, available from Solvay Chemicals, Inc.; Hetoxide GT-80®, available from Global-Seven, Inc.; Lexemul BEO®, available from Inolex Chemical Co.; Polyglycerol-3®, available from Solvay Chemicals, Inc.; Redicote E Series®, available from Akzo Nobel Surface Chemistry LLC; Simulsol OX 1005L®, available from Seppic Inc.; Stanfax 567®, available from Para-Chem Standard Div.; TA-1618®, available from Procter & Gamble; and Witconol H-31A®, available from Akzo Nobel Surface Chemistry LLC.

Class B Amine Oxides

These include but are not limited to those selected from the list B which is defined as follows:

List B

AO-405®, AO-455® and AO-728 Special®, available from Tomah Products®, Inc.; Barlox 12® and Barlox 14®, available from Lonza Inc.; Burcoxide LO®, available from Burlington Chemical Co.®, Inc.; Caloxamine LO®, available from Pilot Chemical Co.; Chemoxide CAW®, Chemoxide LM-30®, Chemoxide LO® and Chemoxide MO®, which are available from Chemron Corp.; Colalux CAO-35® and Colalux LO®, available from Colonial Chemical Co.; DeMox CAPO®, DeMox CSG-30®, DeMox LAO®, available from DeForest Enterprises, Inc.; Emcol L®, available from Crompton Corp.; Empigen OB® and Empigen OS/A®, available from Huntsman LLC; Foamox CDO®, Foamox DMM® and Foamox DMS®, available from Alzo International, Inc.; Genaminox KC® and Genaminox LA®, available from Clariant Corporation; Hartofoam SAO® Hartox DMCD®, available from Hart Chemical Corp.; Lipowax DAT® and Lipowax PB Pastilles®, available from Lipo Chemicals, Inc.; Mackamine C8®, Mackamine C10®, Mackamine C14®, Mackamine CAO®, Mackamine CO®, Mackamine LO®, Mackamine O2®, Mackamine SAO® and Mackamine SO®, available from The McIntyre Group; Mazox KCAO®, available from BASF Corp.; Monalac MO®, available from Uniqema; Norfox LDA®, available from Norman, Fox & Co.; Rhodamox LO®, available from Rhodia, Inc.; Schercamox C-AA®, available from Noveon®, Inc.; Schercamox DMA®, Schercamox DML®, Schercamox DMM®, Schercamox DMS® and Tegotens DO®, available from Goldschmidt Chemical Corp.; Tomah AO-14-2®, available from Tomah Products®, Inc.; Triaminox CDO®, available from Tri-Tex Co.®, Inc.; Mazox CDA CG®; and Standamox CAW®;

Class C: Block Polymers

These are polymers with the structure A-B-A', wherein A and A' are polyethylene chains of 1 or more ethylene units, and B is a polypropylene chain of one or more propylene units. Generally, A and A' are approximately the same length.

In one embodiment, A and A' contain from about 2 to about 200 ethylene units.

In another embodiment, A and A' contain from about 5 to about 100 ethylene units.

In another embodiment, A and A' contain about 7 to about 15 ethylene units.

In another embodiment, A and A' contain about 7, about 8, or about 12 ethylene units.

In another embodiment, B contains from about 25 to about 100 propylene units.

In another embodiment, B contains from about 30 to about 55 propylene units.

In another embodiment, B contains about 30, about 34, or about 54 propylene units.

In another embodiment, the molecular weight is from about 1000 to about 20000.

In another embodiment, the molecular weight is from about 2000 to about 10000.

In another embodiment, the molecular weight is about 2500, about 3000, about 3800, or about 8400.

These include but are not limited to those selected from the list C which is defined as follows: List C, Poloxalene:
wherein A has about 12 ethylene oxide units, B has about 34 propylene oxide units, A' has about 12 ethylene oxide units, and the average molecular weight is about 3000.

Poloxamer 182:
wherein A has about 8 ethylene oxide units, B has about 30 propylene oxide units, A' has about 8 ethylene oxide units, and the average molecular weight is about 2500

Poloxamer 188:
wherein A has about 75 ethylene oxide units, B has about 30 propylene oxide units, A' has about 75 ethylene oxide units, and the average molecular weight is about 8400.

Poloxamer 331:
wherein A has about 7 ethylene oxide units, B has about 54 propylene oxide units, A' has about 7 ethylene oxide units, and the average molecular weight is about 3800; and AL 2070®, available from Uniqema; Antarox 17-R-2®, Antarox 25-R-2®, Antarox 31-R-1®, Antarox P-84®, and Antarox P-104/H®, available from Rhodia, Inc.; Arnox BP-Series®, available from Crompton Corp.; Chemonic 435®, Chemonic D-25®, and Chemonic PL Series®, available from Chemron Corp.; Ethox L-121®, and Ethox L-122®, available from Ethox Chemicals, LLC; Genapol PF-10®, Genapol PF-20® and Genapol PF-40A®, available from Clariant Corporation; Norfox 2-LF®, available from Norman, Fox & Co.; Pluronic, available from BASF; Simulsol NW 342®, available from Seppic Inc.; T-Det BP-1®, T-Det XD® and T-Det XH®, available from Harcros Chemicals Inc.; Triton CF-32®, available from Dow Chemical Company; Witconol 171®, Witconol 324®, Witconol 324D® and Witconol PD-2000®, available from Akzo Nobel Surface Chemistry LLC; Chemal BP 261®; Chemal BP 262®; Chemal BP 3172®; and Chemal BP 3174®; Pluronic 10R5®; Pluronic 17R2®; Pluronic 17R4®; Pluronic 25R2®; Pluronic 25R4®; Pluronic 31R1®; Pluronic F108®; Pluronic F127®; Pluronic F38®; Pluronic F68®; Pluronic F68LF®; Pluronic F77®; Pluronic F87®; Pluronic F88®; Pluronic F98®; Pluronic L10®; Pluronic L101®; Pluronic L121®; Pluronic L31®; Pluronic L35®; Pluronic L43®; Pluronic L44®; Pluronic L61®; Pluronic L62®; Pluronic L62D®; Pluronic L62LF®; Pluronic L64®; Pluronic L81®; Pluronic L92®; Pluronic P103®; Pluronic P104®; Pluronic P105®; Pluronic P123®; Pluronic P65®; Pluronic P84® and Pluronic P85®; Surfonic POA-17R2®; and Surfonic POA-25R2®; Tetronic 1107®; Tetronic 1307®; Tetronic 150R1®; Tetronic 304®; Tetronic 701®; Tetronic 901®; Tetronic 904®; Tetronic 908®; and Tetronic 90R4®;

Class D: Carboxylated Alcohol or Alkylphenol Ethoxylates,
These include but are not limited to those selected from the list D which is defined as follows List D:
Emcol CN-6®, available from Crompton Corp.; Ethcarb®, available from Ethox Chemicals, LLC; Gemtex WNT-Conc®, available from Finetex Inc.; Incrodet TD7-C®, available from Croda Inc.; Marlinat CM 105/80®, Marlowet 1072; Marlowet 4530®, Marlowet 4530 LF®, Marlowet 4534®, Marlowet 4538®, Marlowet 4539®, Marlowet 4539 LF and Marlowet 4541®, available from Sasol North America Inc.; Miranate LEC-80®, available from Rhodia, Inc.; Sandopan B®, Sandopan B Modified®, and Sandopan LS-24 Gel®, available from Clariant Corporation; Surfine T-A®, and Surfine AZI-A, available from Finetex Inc.;

Class E: Carboxylic Acids/Fatty Acids,
These include but are not limited to those selected from the list E which is defined as follows List E:
Saturated carboxylic acids, which have no C═C moieties and include, but are not limited to, myristic acid, palmitic acid, stearic acid, arachidic acid, behenic acid, lignoceric acid.

Unsaturated carboxylic acids, including, but not limited to, the following:
monounsaturated carboxylic acids, which have one C═C group such as palmitoleic acid, oleic acid, and nervonic acid; diunsaturated carboxylic acids, which have two C═C groups, such as linoleic acid;
triunsaturated carboxylic acids, which have three C═C groups, such as α-linolenic acid and γ-linolenic acid;
tetraunsaturated carboxylic acids, which have four C═C groups, such as arachidonic acid; and
pentaunsaturated carboxylic acids, which have five C═C groups, such as eicosapentaenoic acid.

A carboxylic acid with an even number of carbon atoms is a fatty acid, for example:
Lauric Acid has 12 carbon atoms.
Some fatty acids have 14 carbon atoms such as myristic acid.
Some fatty acids have 16 carbon atoms such as palmitic and palmitoleic acid.
Some fatty acids have 18 carbon atoms such as stearic acid, oleic acid, linoleic acid, α-linolenic a, and γ-linolenic acid.
Some fatty acids have 20 carbon atoms such as eicosapentaenoic acid.
Some fatty acids have 22 carbon atoms such as arachidic acid.
Some fatty acids have 24 carbon atoms such as lignoceric acid and nervonic acid.

Specific examples include Colaterge RAM®, and Colatrope INC®, available from Colonial Chemical Co.; Crodacid B®, available from Croda Inc.; DeTrope CA-100®, available from DeForest Enterprises, Inc.; Latol MTO®, available from Georgia-Pacific Corp.; Lumulse CC-33 K®, available from Lambent Technologies Corp.; Mulls 2218®, available from Bernel Chemical Co.®, Inc.; OL-600®, OL-800®, R-910®, and S-210®, available from Procter & Gamble; Sandopan DTC Acid®, Sandopan LS 24 N®, and Sandopan MA-18®, available from Clariant Corporation;

Class F: Ethoxylated Alcohols
These include but are not limited to those selected from the list F which is defined as follows:
List F:
Ethoxylates of linear alcohols having from about 6 to about 20 carbon atoms.
In one embodiment, the linear alcohol has from about 10 to about 16 carbon atoms.
In another embodiment, the ethoxylated alcohol has from about 1 to about 100 ethylene oxide units.
In another embodiment, the ethoxylated alcohol has from about 1 to about 50 ethylene oxide units.
In another embodiment, the ethoxylated alcohol has from about 5 to about 50 ethylene oxide units.
In another embodiment, the ethoxylated alcohol has from about 1 to about 20 ethylene oxide units.
In another embodiment, the ethoxylated alcohol has from about 30 to about 50 ethylene oxide units.
Other examples include but are not limited to the following:
Acdsee 799®, available from Akzo Nobel Surface Chemistry LLC; Acdsee 799®, available from Crompton Corp.; Alfonic 610-3.5®, Alfonic 810-2®, Alfonic 810-6®, Alfonic 1012-3®, Alfonic 1012-5®, Alfonic 1216CO-1.5®, Alfonic 1216CO-7®, Alfonic 1412-3®, and Alfonic 1412-7®, which are available from Sasol North America Inc.; Arlasolve 200®, and Arlasolve 200 Liquid®, available from Uniqema; Armix 180-C®, and Armix 183®, available from Crompton Corp.; Armul 2404®, available from Akzo Nobel Surface Chemistry LLC; Armul 2404®, available from Crompton Corp.; Atlas EMJ-C®, available from Atlas Refinery Inc.; Atlas G-2109®, Atlas G-3886®, and Atlas G-3890®, available from Uniqema; Bio Soft E-200®, Bio Soft E-300®, Bio Soft E-400®, Bio Soft EN 600®, Bio Soft TD-400 and Bio Soft TD-630®, available from Stepan Canada Inc.; Brij 30®, Brij 52®, Brij 56®, Brij 58®, Brij 72®, Brij 76®, Brij 78®, Brij 93®, Brij 97®, Brij 98®, Brij 700®, Brij 700 S®, Brij 721®, and Brij 721 S®, available from Uniqema; Burcoterge CDG®, available from Burlington Chemical Co.®, Inc.; Canasol AT 600®, Canasol AT 800®, Canasol AT 1200®, Canasol BJ 35®, Canasol BJ 36®, Canasol BJ 52®, Canasol BJ 58®, Canasol BJ 72®, Canasol BJ 78®, Canasol BJ 98®, and Canasol BJ 307®, available from Canamex Quimicos S.A de C.v; Cerfak 1400®, available from Houghton International Inc.; Cetomacrogol 1000 BP®, available from Croda Inc.; Chemonic C-2®, Chemonic C-10®, Chemonic C-20®, Chemonic CT-12®, Chemonic CT-20®, Chemonic CT-30®, Chemonic CT-55®, Chemonic G-7®, Chemonic G-26®, Chemonic L-4®, Chemonic L-7®, Chemonic L-12®, Chemonic L-23®, Chemonic 0-2®, Chemonic 0-5®, Chemonic 0-10®, Chemonic 0-20®, Chemonic S-2®, Chemonic S-10®, and Chemonic S-20®, available from Chemron Corp.; Colamulse FE®, available from Colonial Chemical Co.; Cremophor A 20®, and Cremophor SA 2®, available from BASF Corp.; Dehydol 100®, and Dehydol 0-4®, available from Cognis Canada Corp.; Delonic C-18®, available from DeForest Enterprises, Inc.; DeSonic 6T®, DeSonic 9D®, DeSonic 9T®, DeSonic 12D®, DeSonic 12T®, DeSonic 15T®, and DeSonic TDA-9®, available from Crompton Corp.; DeThox GLG-7®, DeThox GLG-26®, DeThox LA-4®, DeThox LA-23®, and DeThox SA-80®, available from DeForest Enterprises, Inc.; Disponil O5®, available from Cognis Corporation; Eccoterge EO-41B®, available from Eastern Color & Chemical Co.; Empilan KA2.5/90®, Empilan KA5/90®, Empilan KM-20®, Empilan KM-50®, and Empilan L-23®, available from Huntsman LLC; Ethylan 25-3®, Ethylan 1204®, Ethylan DA-4®, Ethylan LA-230®, Ethylan SN®, Ethylan TD-60®, Ethylan TD-100®, and Ethylan TD-1407®, available from Akzo Nobel Surface Chemistry LLC; Eumulgin B1®, Eumulgin B2®, Eumulgin B3®, and Eumulgin 0-10®, available from Cognis Canada Corp.; Flo Mo 80/20®, and Flo Mo Low Foam®, which are available from Crompton Corp.; Forlan C-24®, available from RITA Corp.; Genapol 1454®, Genapol BA-020®, Genapol BA-040®, Genapol C-100®, Genapol DA 060®, Genapol HS 020®, Genapol HS 200®, Genapol ID-040®, Genapol ID-060®, Genapol ID-090®, Genapol LA 010®, Genapol LA 020®, Genapol LA 030®, Genapol LA 040®, Genapol LA 050®, Genapol LA 060®, Genapol LA 070®, Genapol LA 070S®, Genapol LA 230®, Genapol O 020®, Genapol O 050®, Genapol O 100®, Genapol O 200®, Genapol SA 030®, Genapol SA 120®, Genapol T-020®, Genapol UD-030®, Genapol UD-050®, Genapol UD-070®, Genapol UD-079®, Genapol UD-080®, Genapol UD-110®, Genapol X 030®, Genapol X 050®, Genapol X 060®, Genapol X 070®, Genapol X 080®, Genapol X 100®, and Genapol X159®, available from Clariant Corporation; Generol 122 E5®, and Generol 122 E25®, available from Cognis Canada Corp.; Hostacerin T-3®, available from Clariant Corporation; Iconol LF 110®, available from BASF Corp.; Incropol CS-20®, available from Croda Inc.; Lexemul CS-20®, available from Inolex Chemical Co.; Liponic EG-1®, Lipowax D®, Lipowax G®, Lipowax NI®, Lipowax P®, Lipowax P-31®, and Lipowax PR®, available from Lipo Chemicals, Inc.; Lumulse CS-20®, available from Lambent Technologies Corp.; Macol CSA-20®, available from BASF Corp.; Marlox B 24/50®, available from Sasol North America Inc.; Mazawet 77®, available from BASF Corp.; Norfox 1713®, Norfox 2579®, and Norfox Lo Foam®, available from Norman, Fox & Co.; Promulgen D®, and Promulgen G®, available from Amerchol Corp.; Renex 30®, and Renex 36®, available from Uniqema; Rhodasurf A 24®, Rhodasurf AAE-10®, Rhodasurf BEH-25®, Rhodasurf BEH-40®, Rhodasurf DA 530®, Rhodasurf DA 630®, Rhodasurf DA 639®, Rhodasurf LAN-23®, Rhodasurf ON-870®, Rhodasurf ON-877®, and Rhodasurf TB-970 FLK®, available from Rhodia, Inc.; Ritacet-20®, Ritachol 1000®, Ritachol 2000®, Ritachol 5000®, and Ritox 35®, available from RITA Corp.; Surfonic DA-4®, Surfonic DA-6®, Surfonic L46-7®, and Surfonic POA®, available from Huntsman LLC; Synthrapol KB®, available from Uniqema; Teginacid®, Teginacid C®, and Tegotens EC 11®, available from Goldschmidt Chemical Corp.; Tinegal NA®, available from Ciba Specialty Chemicals Corp.; Tomadol 400®, Tomadol 600®, and Tomadol 900®, available from Tomah Products®, Inc.; Uniperol O®, available from BASF Corp.; Witconol SN Series®, available from Crompton Corp.; T-Det EPO-64®; T-Det N-1.5®; T-Det N-10.5®; T-Det N-100®; T-Det N-1007®; T-Det N-12®; T-Det N-14®; T-Det N-20®; T-Det N-30®; T-Det N-307®; T-Det N-4®; T-Det N-40®; T-Det N-407®; T-Det N-50®; T-Det N-507®; T-Det N-6®; T-Det N-70®; T-Det N-8®; T-Det N-9.5®; T-Det O-12®; Abex 2515®; Abex 2525/40®; Abex 2535®; Abex 2545®; Alfonic 1216CO-9®; Alfonic 1412-3®; Alfonic TDA-12®; Alfonic TDA-3®; Alfonic TDA-4®; Alfonic TDA-6®; Alfonic TDA-7®; Alfonic TDA-8®; Alfonic TDA-9®; Ameroxol OE-10®; Ameroxol OE-2®; Ameroxol OE-20®; Armix 176®; Armix 180-C®; Armix 183®; Brij 35®; Brij 35 Liquid®; Brij 35 SP®; Canasol MJ 2109®; Canasol MJ 52®; Canasol R 3600®; Canasol R 3603®; Canasol R 4000 H®; Chemal DA-4®; Chemal DA-6®; Chemal DA-9®; Chemal LA-23®; Chemal LA-4®; Chemal LA-9®; Chemal OA-20G®; Chemal OA-5®; Chemal OA-9®; Chemal TDA-12®; Chemal TDA-15®; Chemal TDA-3®; Chemal TDA-6®; Chemal TDA-9®; DeSonic TDA-9®; Ethal EH-2®; Ethal EH-5®; Ethal OA-23®; Ethosperse CA-20®; Ethosperse LA-12®; Ethosperse LA-23®; Ethosperse LA-4®; Ethylan SN-120®; Ethylan SN-70®; Ethylan SN-90®; Generol 122 E25®; Hetoxol C-24®; Hetoxol CA-10®; Hetoxol CA-2®; Hetoxol CA-20®; Hetoxol CAWS®; Hetoxol CD-3®; Hetoxol CD-4®; Hetoxol CS-15®; Hetoxol CS-20®; Hetoxol CS-20D®; Hetoxol CS-25®; Hetoxol CS-50®; Hetoxol CS-9®; Hetoxol CSA-15®; Hetoxol D®; Hetoxol G®; Hetoxol J®; Hetoxol L®; Hetoxol L-23®; Hetoxol L-4®; Hetoxol L-9®; Hetoxol LS-9®;

Hetoxol M-3®; Hetoxol OA-10 Special®; Hetoxol OA-20 Special®; Hetoxol OA-3 Special®; Hetoxol OA-5 Special®; Hetoxol OL-10®; Hetoxol OL-2®; Hetoxol OL-23®; Hetoxol OL-4®; Hetoxol OL-40®; Hetoxol OL-5®; Hetoxol PLA®; Hetoxol SP-15®; Hetoxol STA-10®; Hetoxol STA-2®; Hetoxol STA-30®; Hetoxol TD-12®; Hetoxol TD-18®; Hetoxol TD-3®; Hetoxol TD-6®; Hetoxol TD-9®; Hetoxol TDEP-15®; Hetoxol TDEP-63®; Iconol 24-12®; Iconol 24-23®; Iconol 24-4®; Iconol DA-4®; Iconol DA-6®; Iconol TDA-10®; Iconol TDA-3®; Iconol TDA-6®; Iconol TDA-8-90%®; Iconol TDA-9®; Lexemul CS-20®; Lipocol C-10®; Lipocol C-2®; Lipocol C-20®; Lipocol L-12®; Lipocol L-23®; Lipocol L-4®; Lipocol O-10®; Lipocol O-2®; Lipocol O-20®; Lipocol O-5®; Lipocol S-10®; Lipocol S-2®; Lipocol S-20®; Lipocol SC-15®; Lipocol SC-20®; Lipocol SC-4®; Lipocol TD-12®; Marlox B 24/80®; Myrj 45®; Myrj 52®; Myrj 52S®; Myrj 53®; Myrj 59®; Plurafac A-38®; Plurafac B-25-5®; Plurafac B-26®; Plurafac D-25®; Plurafac LF 131®; Plurafac LF 4030®; Plurafac LF 7000®; Plurafac RA-20®; Plurafac RA-30®; Plurafac RA-40®; Rhodasurf BC-420®; Rhodasurf BC-610®; Rhodasurf BC-630®; Rhodasurf BC-720®; Rhodasurf BC-840®; Rhodasurf L 1®; Rhodasurf L 12®; Rhodasurf L 2®; Rhodasurf L 20®; Rhodasurf L 3®; Rhodasurf L 30®; Rhodasurf L 4®; Rhodasurf L 50®; Rhodasurf L 7/90®; Rhodasurf LA-3®; Rhodasurf LA-7®; Rhodasurf LAN-23®; Rhodasurf ON-870®; Rhodasurf ON-877®; Rhodasurf TDA-8/5®; Ritapro 100®; Ritapro 165®; Ritapro 200®; Ritapro 300®; Ritoleth 10®; Ritoleth 2®; Ritoleth 20®; Ritoleth 5®; Solulan 16®; Solulan 75®; Solulan C-24®; Solulan L-575®; Surfonic TDA-11®; Surfonic TDA-3B®; Surfonic TDA-6®; Surfonic TDA-6/88®; Surfonic TDA-8®; Surfonic TDA-8/90®; Surfonic TDA-9®; T-Det A106®; T-Det A109®; T-Det A136®; T-Det A139®; T-Det A2412®; T-Det A243®; T-Det A247®; T-Det A249®; T-Det A467®; T-Det COE®; T-Det DD-10®; T-Det DD-5®; T-Det DD-7®; T-Det EPO-104®; T-Det EPO-61®; T-Det EPO-62®; T-Det O-165®; T-Det O-307®; T-Det O-40®; T-Det O-407®; T-Det O-6®; T-Det O-8®; T-Det O-9®; Tergitol 15-S-12®; Tergitol 15-S-15®; Tergitol 15-S-20®; Tergitol 15-S-20 (80AQ)®; Tergitol 15-S-3®; Tergitol 15-S-30®; Tergitol 15-S-40®; Tergitol 15-S-40 (70AQ)®; Tergitol 15-S-5®; Tergitol 15-S-7®; Tergitol 15-S-9®; Tergitol L-101®; Tergitol L-61®; Tergitol L-62®; Tergitol L-64®; Tergitol L-81®; Tergitol NP-10®; Tergitol NP-11®; Tergitol NP-12®; Tergitol NP-13®; Tergitol NP-15®; Tergitol NP-30®; Tergitol NP-30 (70 AQ)®; Tergitol NP-4®; Tergitol NP-40®; Tergitol NP-40 (70 AQ)®; Tergitol NP-50 (70 AQ)®; Tergitol NP-55 (70 AQ)®; Tergitol NP-6®; Tergitol NP-7®; Tergitol NP-70 (70 AQ)®; Tergitol NP-8®; Tergitol NP-9®; Tergitol NP-9.5®; Tergitol TMN-10®; Tergitol TMN-3®; Tergitol TMN-6®; Tergitol XD®; Tergitol XH®; Tergitol XJ®; Tomadol 1-3®; Tomadol 1-5®; Tomadol 1-7®; Tomadol 23-1®; Tomadol 23-3®; Tomadol 23-5®; Tomadol 23-6.5®; Tomadol 25-12®; Tomadol 25-3®; Tomadol 25-7®; Tomadol 25-9®; Tomadol 45-13®; Tomadol 45-2.5®; Tomadol 45-7®; Tomadol 91-2.5®; Tomadol 91-6®; Tomadol 91-8®; Volpo S-10®; Volpo S-2®; Volpo S-20®; Volpo-10®; Volpo-20®; Volpo-3®; and Volpo-5®;

Class G: Ethoxylated Alkylphenols

These are alkylphenols that are ethoxylated, i.e. the phenolic OH is replaced with $(OCH_2CH_2O)_nH$. These include but are not limited to those selected from the list G which is defined as follows:

List G octylphenol ethoxylate, i.e. $C_8H_{17}Ph(OCH_2CH_2O)_nH$.
nonylphenol ethoxylate, i.e. $C_9H_{19}Ph(OCH_2CH_2O)_nH$.
alkylphenols of the above formula wherein n is about 1 to about 100.
alkylphenols of the above formula wherein n is about 1 to about 50.
alkylphenols of the above formula wherein n is about 9 to about 15.

Octyl Phenol 1.5 Mole Ethoxylate (i.e. n is an average of about 1.5); Octyl Phenol 5 Mole Ethoxylate; Octyl Phenol 7 Mole Ethoxylate; Octyl Phenol 9 Mole Ethoxylate; Octyl Phenol 12 Mole Ethoxylate; Octyl Phenol 40 Mole Ethoxylate; Nonyl Phenol 1.5 Mole Ethoxylate; Nonyl Phenol 4 Mole Ethoxylate; Nonyl Phenol 6 Mole Ethoxylate; Nonyl Phenol 9 Mole Ethoxylate; Nonyl Phenol 10 Mole Ethoxylate; Nonyl Phenol 10.5 Mole Ethoxylate; Nonyl Phenol 12 Mole Ethoxylate; Nonyl Phenol 15 Mole Ethoxylate; Nonyl Phenol 15 Mole Ethoxylate; Nonyl Phenol 30 Mole Ethoxylate; and Nonyl Phenol 40 Mole Ethoxylate;

Specific examples include Antarox LF-222®, available from Rhodia, Inc.; Atlox 775®, available from Uniqema; Caloxylate N-9®, available from Pilot Chemical Co.; Canasol NF-1000®, Canasol NF-3000®, Canasol NF-3070®, Canasol OF 1670®, Canasol OF 2570®, and Canasol OF 4070®, available from Canamex Quimicos S.A de C.v; Chemax DNP-8®, Chemax DNP-18®, and Chemax DNP-150/50®, available from Chemax Performance Solutions; DeSonic 1.5N®, DeSonic 4N®, available from Crompton Corp.; DeSonic 5N®, DeSonic 6D®, DeSonic 6N®, DeSonic 7N®, DeSonic 9N®, DeSonic 10D®, DeSonic 11N®, DeSonic 12N®, DeSonic 15N®, and DeSonic 20N®, available from Crompton Corp.; Eccoscour RC®, and Eccoterge EO-100®, available from Eastern Color & Chemical Co.; Emulsifier 632/90%®, available from Ethox Chemicals, LLC; Geronol AG-821®, available from Rhodia, Inc.; Gradonic N-95®, available from Graden Chemical Co. Inc.; Hetoxide NP-4®, available from Global-Seven, Inc.; Hetoxide NP-30®, available from Global-Seven, Inc.; Hostapal N-100®, and Hostapal N-110®, available from Clariant Corporation; Igepal CTA-639W®, Igepal DAP-9®, Igepal OD-410®, and Igepal SS-837®, available from Rhodia, Inc.; Lipocol NP-9 USP®, available from Lipo Chemicals, Inc.; Macol DNP-10®, available from BASF Corp.; Marlophen NP 5®, and Marlophen P 1®, available from Sasol North America Inc.; Surfonic NB®, Surfonic OPB-307®, and Surfonic OPB-407®, available from Huntsman LLC; Syn Fac 334®, and Syn Fac 8216®, available from Milliken Chemical; Triton N-57®, available from Dow Chemical Company; Trycol 6956®, Trycol 6961®, Trycol 6964®, Trycol 6969®, and Trycol 6974®, available from Cognis Corporation; Witbreak DRB-127®, available from Akzo Nobel Surface Chemistry LLC; Witbreak DRB-127®, available from Crompton Corp.; and Witconol NP Series®, available from Akzo Nobel Surface Chemistry LLC; Delonic NPE-100®; Delonic NPE-30®; Delonic NPE-40®; Delonic OPE-10®; Delonic OPE-12®; Delonic OPE-30®; Delonic OPE-40®; Delonic OPE-5®; Delonic OPE-7.5®; DeSonic S-100®; DeSonic S-114®; DeSonic S-405®; DeSonic S-45®; Igepal CA-210®; Igepal CA-407®; Igepal CA-420®; Igepal CA-520®; Igepal CA-620®; Igepal CA-630®; Igepal CA-720®; Igepal CA-877®; Igepal CA-887®; Igepal CA-897®; Igepal CO-210®; Igepal CO-430®; Igepal CO-520®; Igepal CO-530®; Igepal CO-610®; Igepal CO-630®; Igepal CO-630 Special®; Igepal CO-660®; Igepal CO-710®; Igepal CO-720®; Igepal CO-730®; Igepal CO-738®; Igepal CO-850®; Igepal CO-880®; Igepal CO-887®; Igepal CO-890®; Igepal CO-897®; Igepal CO-970®; Igepal CO-977®; Igepal CO-987®; Igepal CO-990 FLK®; Igepal CO-997®; Igepal DM-430®; Igepal DM-530®; Igepal DM-710®; Igepal DM-730®; Igepal DM-880®; Igepal DM-970 FLK®; Igepal OD-410®; Igepal RC-520®; Igepal RC-620®; Igepal RC-630®; Norfox NP-12®; Norfox NP-4®; Norfox NP-6®; Norfox NP-887®; Norfox NP-9®; Norfox NP-977®; Norfox OP-100®; Norfox OP-102®; Norfox OP-114®; Norfox OP-45®; Surfonic N-10®; Surfonic N-100®; Surfonic N-102®; Surfonic N-120®; Surfonic N-150®; Surfonic N-200®; Surfonic N-300®; Surfonic N-31.5®; Surfonic N-40®; Surfonic N-400®; Surfonic N-60®; Surfonic N-85®; Surfonic N-95®; Surfonic NB-18®; Surfonic NB-23®; Surfonic NB-25®; Surfonic NB-307®; Surfonic NB-31®; Surfonic NB-41®; Surfonic NB-43®; Surfonic OP-100®; Surfonic OP-120®; Surfonic OP-15®; Surfonic OP-35®; Surfonic OP-70®; Triton X-100®; Triton X-102®; Triton X-114®; Triton X-15®; Triton X-165 (70%)®; Triton X-207®; Triton X-305 (70%)®; Triton X-35®; Triton X-405 (70%)®; Triton X-45®; and Triton X-705 (70%)®;

Class H: Ethoxylated Aryl Phenols,
  These include but are not limited to those selected from the list H which is defined as follows: List H:
  Soprophor BSU®, Soprophor CY/8®, and Soprophor S/25®, available from Rhodia, Inc.; Witconol NIO®, Witconol NIW®, and Witconol S-100®, available from Akzo Nobel Surface Chemistry LLC; Cedepal CA-210®; Cedepal CA-520®; Cedepal CA-630®; Cedepal CA-720®; Cedepal CA-890®; Cedepal CA-897®; Cedepal CO-210®; Cedepal CO-430®; Cedepal CO-530®; Cedepal CO-630®; Cedepal CO-710®; Cedepal CO-730®; Cedepal CO-880®; Cedepal CO-887®; Cedepal CO-890®; Cedepal CO-897®; Cedepal CO-970®; Cedepal CO-977®; Cedepal CO-990®; and Cedepal CO-997®;

Class I: Ethoxylated Fatty Acids,
  These include but are not limited to those selected from the list I which is defined as follows:
List I
ethoxylate chains, i.e. $HO(CH_2CH_2O)_nOH$,
which are esterified to form either:
monoesters, i.e. $RCO_2(CH_2CH_2O)_nOH$, where $RCO_2H$ is a fatty acid; or
diesters, i.e. $RCO_2(CH_2CH_2O)_nC(=O)R$.
  Saturated fatty acids, which have no C=C moieties and include myristic acid, palmitic acid, stearic acid, arachidic acid, behenic acid, lignoceric acid.
    Unsaturated fatty acids, including the following:
    monounsaturated fatty acids, which have one C=C group such as palmitoleic acid, oleic acid, and nervonic acid;
    diunsaturated fatty acids, which have two C=C groups, such as linoleic acid;
    triunsaturated fatty acids, which have three C=C groups, such as α-linolenic acid and γ-linolenic acid;
    tetraunsaturated fatty acids, which have four C=C groups, such as arachidonic acid; and
    Pentaunsaturated fatty acids, which have five C=C groups, such as eicosapentaenoic acid.
  The following may also be used:
Lauric Acid; 14 carbon fatty acids such as myristic acid; 16 carbon fatty acids such as palmitic and palmitoleic acid; 18 carbon fatty acids such as stearic acid, oleic acid, linoleic acid, α-linolenic acid, and γ-linolenic acid; 20 carbon fatty acids such as eicosapentaenoic acid; 22 carbon fatty acids such as arachidic acid; and 24 carbon fatty acids such as lignoceric acid and nervonic acid.
  In one embodiment, n is from about 2 to about 100.
  In another embodiment, n is from about 5 to about 50.
  In another embodiment, n is from about 30 to 50.
  Specific examples include Aldo PGHMS®, available from Lonza Inc.; Alkamuls TO-15/HR®, available from Rhodia, Inc.; Armotan AL-69-66®, available from Akzo Nobel Surface Chemistry LLC; Cerasynt 840®, and Cerasynt 945®, available from International Specialty Products/IS; Crystal Inhibitor No. 5®, available from Harcros Chemicals Inc.; DeThox Acid L-9®, and DeThox Acid S-8®, available from DeForest Enterprises, Inc.; Ethofat 242/25®, available from Akzo Nobel Surface Chemistry LLC; Hydropalat 65®, available from Cognis Corporation; Lipo EGMS®, Lipopeg 2 DL®, Lipopeg 4 DL®, Lipopeg 4-L®, Lipopeg 39-S®, Lipopeg 4-S®, Lipopeg 10-S®, Lipopeg 100-S®, and Lipopeg 6000 DS®, available from Lipo Chemicals, Inc.; Lumulse 40-L®, Lumulse 40-S®, Lumulse 42-L®, Lumulse 42-S®, Lumulse 100-S®, and Lumulse 602-S®, available from Lambent Technologies Corp.; Magrabar PGE-20-0®, Magrabar PGE-20L®, Magrabar PGE-20T®, Magrabar PGE-22-0®, Magrabar PGE-22L®, Magrabar PGE-22T®, Magrabar PGE-40-0®, Magrabar PGE-40L®, Magrabar PGE-40T®, Magrabar PGE-42-0®, Magrabar PGE-42L®, Magrabar PGE-42T®, Magrabar PGE-60-0®, Magrabar PGE-60L®, Magrabar PGE-60T®, Magrabar PGE-62-0®, Magrabar PGE-62L®, and Magrabar PGE-62T®, available from Magrabar Chemical Corp.; Mapeg S-40K®, available from BASF Corp.; Marlowet OTS®, available from Sasol North America Inc.; Naturechem PGR®, available from CasChem®, Inc.; PG No. 4®, available from Hart Chemical Corp.; Renex 20®, available from Uniqema; Ritox 52®, Ritox 53®, and Ritox 59®, available from RITA Corp.; Surfax 8916/A®, available from Houghton International Inc.; Tego Acid S 40 P®, and Tego Acid S 100 P®, available from Goldschmidt Chemical Corp.; Tween 20®, available from Uniqema; Volpo 131®, available from Croda Inc.; Alkamuls 400-MO/E®; DeThox Acid 0-14®; DeThox Acid 0-16®; DeThox Acid O-9®; DeThox Acid TO-14®; DeThox Acid TO-16.5®; DeThox Acid TO-8.5®; Emerest 2704®; Emerest 2712®; Emerest 2715®; Ethox MA-8®; Ethox MI-14®; Ethox ML-14®; Ethox ML-5®; Ethox MO-14®; Ethox MO-9®; Ethox MS-14®; Ethox MS-23®; Ethox MS-40®; Ethox MS-8®; Ethox TO-16®; Ethox TO-8®; Flexricin 13®; Flexricin 15®; Genapol 1261®; Lumulse 40-O K®; Lumulse 42-O K®; Lumulse GMT-40®; Lumulse PEG 1450®; Lumulse PEG 1450 NF®; Lumulse PEG 8000®; Lumulse PGO®; Lumulse POE (2) Oleyl Amine®; Magrabar PGO-104®; Mapeg 200 ML®; Mapeg 400 MO®; Mapeg 400 MOT®; Mapeg 400DO®; Mapeg 400DOT®; Mapeg 600DOT®; Marlox FK 86®; Marlox MO 154®; Surfonic L12-3®; Surfonic L12-6®; Surfonic L12-8®; Surfonic L24-12®; Surfonic L24-2®; Surfonic L24-22®; Surfonic L24-3®; Surfonic L24-4®; Surfonic L24-5®; Surfonic L24-7®; Surfonic L24-7.1®; Surfonic L24-9®; Surfonic LF-17®; Surfonic LF-18®; Surfonic LF-37®; Surfonic LF-41®; Surfonic LF-42®; Surfonic LF-47®; Surfonic LF-68®; Surfonic P1®; Surfonic P3®; Surfonic P5®; and Surfonic P6®;

Class J: Ethoxylated Fatty Esters or Oils (Animal & Veg.).

These are the products which result from reacting ethylene oxide with a fatty ester or an oil. When a fatty oil is used, the products is a mixture of ethoxylates of the fatty acids present in the oil, ethoxylates of glycerine, ethoxylates of mono and diglycerides, and the like.

Specific examples include, but are not limited to, those selected from the list J which is defined as follows:

List J:

Ethoxylates of the following oils: Anise oil, Castor oil, Clove oil, Cassia oil, Cinnamon oil; Almond oil, Corn oil, Arachis oil, Cottonseed oil, Safflower oil, Maize oil, Linseed oil, Rapeseed oil, Soybean oil, Olive oil, Caraway oil, Rosemary oil, Peanut oil, Peppermint oil, Sunflower oil, Eucalyptus oil and Sesame oil; Coriander oil, Lavender oil, Citronella oil, Juniper oil, Lemon oil, Orange oil, Clary sage oil, Nutmeg oil, Tea tree oil, coconut oil, tallow oil, and lard;

In one embodiment, from 1 to about 50 moles of ethylene oxide is used per mole of the oil triglyceride.

In another embodiment, from about 30 to about 40 moles of ethylene oxide is used per mole of the oil triglyceride.

Ethylene oxide may also react with a fatty acid ester with a formula $RCO_2R'$ to form $RCO_2(CH_2CH_2O)_nR'$. Thus, surfactants having the formula $RCO_2(CH_2CH_2O)_nR'$, where $RCO_2H$ is a fatty acid and R' is alkyl having from 1 to 6 carbons are contemplated.

In one embodiment, R' is methyl.

In another embodiment, $RCO_2H$ is Lauric Acid; a 14 carbon fatty acid such as myristic acid; a 16 carbon fatty acid such as palmitic and palmitoleic acid; an 18 carbon fatty acids such as stearic acid, oleic acid, linoleic acid, α-linolenic acid, and γ-linolenic acid; a 20 carbon fatty acids such as eicosapentaenoic acid; a 22 carbon fatty acids such as arachidic acid; or a 24 carbon fatty acids such as lignoceric acid and nervonic acid. Specific surfactants include Acconon 6-C10®, Acconon CC-6®, and Acconon CO-7®, available from Abitec Corporation; Aldosperse 40/60 FG®, Aldosperse ML-23®, and Aldosperse MS-20 FG®, available from Lonza Inc.; Alkamuls EL-620®, Alkamuls EL-719®, and Alkamuls EL-985®, available from Rhodia, Inc.; Arlatone G®, Arlatone T®, Atlas G-1045A®, Atlas G-1086®, Atlas G-1087®, Atlas G-1089®, Atlas G-1096®, Atlas G-1292®, Atlas G-1293®, Atlas G-1300®, and Atlas G-7076®, available from Uniqema; Capmul EMG®, available from Abitec Corporation; Chemonic CO-40®, Chemonic LI-3®, and Chemonic LI-7®, available from Chemron Corp.; Cirrasol GM®, available from Uniqema; Cremophor CO 40®, Cremophor CO 410®, Cremophor EL®, Cremophor GC7®, and Cremophor RH-40®, available from BASF Corp.; Crovol A-40®, Crovol A-70®, Crovol M-70®, and Crovol PK-70®, available from Croda Inc.; Cutina E-24®, available from Cognis Canada Corp.; Dacospin 12-R®, and Dehymuls HRE-7®, available from Cognis Corporation; DeSonic 30C®, DeSonic 36C®, and DeSonic 40C®, available from Crompton Corp.; Durfax 60®, Durfax 65®, Durfax 80®, and Durfax EOM®, available from Loders Croklaan U.S.A.; Eccoterge NF-2®, available from Eastern Color & Chemical Co.; Emulpon CO-360®, and Emulpon CO-550®, available from Akzo Nobel Surface Chemistry LLC; Emulsogen EL®, Emulsogen HCO 040®, and Emulsogen HCO 060®, available from Clariant Corporation; Emulsynt 1055®, available from International Specialty Products/IS; Ethox 3095®, available from Ethox Chemicals, LLC; Eumulgin RO-40®, available from Cognis Canada Corp.; Genapol G-260®, available from Clariant Corporation; Glycosperse L-20®, Glycosperse 0-5®, Glycosperse 0-20®, Glycosperse 0-20 FG®, Glycosperse S-20®, Glycosperse S-20 FG®, Glycosperse TS-20®, and Glycosperse TS-20 FG®, available from Lonza Inc.; Hetan SL®, Hetan SO®, Hetan SS®, Hetoxide C-2®, Hetoxide C-9®, Hetoxide C-15®, Hetoxide C-25®, Hetoxide C-40®, Hetoxide C-200®, Hetoxide C-200-50%®, Hetoxide GC-30®, and Hetoxide HC-60®, available from Global-Seven, Inc.; Ice No. 2®, available from Loders Croklaan U.S.A.; Incrocas 30/40®, available from Croda Inc.; Lexol EC®, and Lexol EO®, available from Inolex Chemical Co.; Lipocol HCO-40®, Lipocol HCO-60®, Lipocol O-3 Special®, Lipopeg 2-L®, Lipopeg 4-DO®, Lipopeg 4-DS®, and Lipovol GTB®, available from Lipo Chemicals, Inc.; Lonzest SML-20®, Lonzest SMO-20®, Lonzest SMS-20®, Lonzest STO-20®, and Lonzest STS-20®, available from Lonza Inc.; Lumulse GR-40®, Lumulse GRH-40®, Lumulse POE (7) GML®, Lumulse POE (12) Glyc®, and Lumulse POE (40) MS KP®, available from Lambent Technologies Corp.; Marlowet 4750®, Marlowet LVS®, Marlowet R 11®, and Marlowet R 40®, available from Sasol North America Inc.; Mazol 80 MGK®, available from BASF Corp.; Nonionic Emulsifier T-9®, available from Werner G. Smith Inc.; Oronal LCG®, available from Seppic Inc.; Polyderm PPI-CO-200®, and Polyderm PPI-CO-40®, available from Alzo International, Inc.; Rewoderm LI 520-70®, available from Goldschmidt Chemical Corp.; Ritapeg 150 DS®, available from RITA Corp.; Softigen 767®, available from Sasol North America Inc.; Surfactol 318®, and Surfactol 365®, available from CasChem®, Inc.; Syn Lube 107®, Syn Lube 728®, Syn Lube 1632H®, and Syn Lube 6277-A®, available from Milliken Chemical; T-Det C-20®, and T-Det C-40®, available from Harcros Chemicals Inc.; Tally 100 Plus®, available from Loders Croklaan U.S.A.; Uniperol EL®, available from BASF Corp.; Acconon E®; Chemax CO-16®; Chemax CO-200/50®; Chemax CO-25®; Chemax CO-30®; Chemax CO-36®; Chemax CO-40®; Chemax CO-5®; Chemax CO-80®; Chemax DNP-150/50®; Chemax DNP-18®; Chemax DNP-8®; Chemax E 200 ML®; Chemax E 200 MO®; Chemax E 400 ML®; Chemax E 400 MO®; Chemax E 600 ML®; Chemax E 600 MO®; Chemax E1000 MO®; Chemax E1000 MS®; Chemax E200 MS®; Chemax E400 MS®; Chemax E600 MS®; Chemax HCO-16®; Chemax HCO-200/50®; Chemax HCO-25®; Chemax HCO-5®; Chemax TO-16®; Chemax TO-8®; Colalube 3409®; Colalube 3411®; Colalube 3413®; Colalube 3414®; Colalube 3415®; Colalube 3416®; Colalube 3417®; DePeg 16-CO®; DePeg 25-CO®; DePeg 30-CO®; DePeg 40-CO®; DePeg 5-CO®; DePeg 80-CO®; Ethox 3095®; Ethox CO-16®; Ethox CO-200®;

Ethox CO-25®; Ethox CO-30®; Ethox CO-36®; Ethox CO-40®; Ethox CO-5®; Hetoxide BN-13®; Hetoxide DNP-4®; Hetoxide DNP-9.6®; Hetoxide G-26®; Hetoxide G-7®; Hetoxide GT-20®; Hetoxide HC-40®; Lipo GMS 450®; Lipo Polyglycol 1000®; Lipo Polyglycol 200®; Lipo Polyglycol 300®; Lipo Polyglycol 3350®; Lipo Polyglycol 400®; Lipo Polyglycol 600®; Surfonic CO-15®; Surfonic CO-25®; Surfonic CO-30®; Surfonic CO-36®; Surfonic CO-42®; Surfonic TX-CCN®; Tagat CH 40®; Tagat CH 60®; Tagat L 2®; Tagat S®; Tagat S 2®; and Tally 100 Plus®;

Class K: Fatty Esters

These include but are not limited to those selected from the list K which is defined as follows:

List K:

fatty acid alkyl esters such as fatty acid methyl esters, such as methyl esters of: Lauric Acid; a 14 carbon fatty acid such as myristic acid; a 16 carbon fatty acid such as palmitic and palmitoleic acid; an 18 carbon fatty acids such as stearic acid, oleic acid, linoleic acid, α-linolenic acid, and γ-linolenic acid; a 20 carbon fatty acids such as eicosapentaenoic acid; a 22 carbon fatty acids such as arachidic acid; or a 24 carbon fatty acids such as lignoceric acid and nervonic acid; and monoglycerides, diglycerides, or mixtures thereof such as those formed by partially saponifying fatty oils, including, but not limited to Anise oil, Castor oil, Clove oil, Cassia oil, Cinnamon oil; Almond oil, Corn oil, Arachis oil, Cottonseed oil, Safflower oil, Maize oil, Linseed oil, Rapeseed oil, Soybean oil, Olive oil, Caraway oil, Rosemary oil, Peanut oil, Peppermint oil, Sunflower oil, Eucalyptus oil and Sesame oil; Coriander oil, Lavender oil, Citronella oil, Juniper oil, Lemon oil, Orange oil, Clary sage oil, Nutmeg oil, Tea tree oil, coconut oil, tallow oil, and lard.

Additionally, monoglycerides, diglycerides, or mixtures thereof may be formed from any combination of the single fatty acids and glycerine.

specific examples include

Actralube-Syn 147®, available from Georgia-Pacific Corp.; Atlas G-1556®, and Atlas G-1564®, available from Uniqema; Atlasol Base Oil S®, available from Atlas Refinery Inc.; Base ML®, and Base MT®, available from Keil Chemical; Cerasynt 303®, available from International Specialty Products/IS; Dermol 1012®, available from Alzo International, Inc.; Kemester 4000®, available from Crompton Corp.; Lactipol S®, available from Canamex Quimicos S.A de C.v; Magrabar PGO®, available from Magrabar Chemical Corp.; Mayco Base BFO®, available from Dover Chemical Corp.; Methyl Linoleate®, available from Hart Chemical Corp.; Pationic 122A®, Pationic 138C®, Pationic CSL®, Pationic ISL®, Pationic SBL®, Pationic SSL®, and Ritasol®, available from RITA Corp.; Tego Alkanol CS 20®, Tego Alkanol L23 P®, Tego Alkanol S2®, and Tego Alkanol S20 P®, available from Goldschmidt Chemical Corp.; Triemulsifier 600 MS®, available from Tri-Tex Co.®, Inc.; Santone 10-10-0®; Santone 3-1-S XTR®; Santone 3-1-SH®; and Santone 8-1-O®;

Class L: Glycerol Esters

These include but are not limited to those selected from the list L which is defined as follows:

List L:

Agro #9 Wint SBO®, available from Lambent Technologies Corp.; Ahcovel Base 700®, available from Uniqema; Aldo HMS FG®, Aldo MLD®, Aldo MLD FG®, Aldo MO FG®, Aldo MS®, Aldo MS FG®, Aldo MS LG FG®, Aldo MSD®, Aldo MSD FG®, Aldosperse O-20 FG®, Aldosperse TS-20 FG®, and Aldosperse TS-40 FG®, available from Lonza Inc.; Arlacel 165®, and Arlacel 186®, available from Uniqema; Capmul GMO®, Capmul GMS®, Caprol 3GO®, Caprol 3GVS®, Caprol 6G2S®, Caprol 10G40®, Caprol 10G100®, Caprol ET®, and Caprol PGE860®, available from Abitec Corporation; Cerasynt 945®, Cerasynt GMS®, Cerasynt Q®, Cerasynt SD®, and Cerasynt WM®, available from International Specialty Products/IS; Chemsperse 14®, available from Chemron Corp.; Cremophor GO-32®, Cremophor GS11®, and Cremophor GS-32®, available from BASF Corp.; Cutina KD-16®, available from Cognis Canada Corp.; Dehymuls PGPH®, available from Cognis Corporation; Dermol DGDIS®, Dermol DGMIS®, Dermol G-76®, Dermol G-7DI®, Dermol NGDI®, and Dermolan GLH®, available from Alzo International, Inc.; Drewmulse GMO®, and Drewpol 3-5-M®, available from Stepan Company; Durlac 100 W®, and Dur-LO®, available from Loders Croklaan U.S.A.; Dynasan 118®, available from Sasol North America Inc.; EC-25®, available from Loders Croklaan U.S.A.; EM 40®, available from Keil Chemical; Emerest 2400®, and Emerest 2452®, available from Cognis Corporation; Empilan G-26®, available from Huntsman LLC; Genapol TSM®, Hostacerin DGI®, Hostacerin DGL®, Hostacerin DGMS®, and Hostacerin DGSB®, available from Clariant Corporation; Ice No. 2®, available from Loders Croklaan U.S.A.; Imwitor 742®, Imwitor 780 K®, and Imwitor 960 Flakes®, available from Sasol North America Inc.; Isolan GI 34®, and Isolan GO 33®, available from Goldschmidt Chemical Corp.; Kemester 1000®, Kemester 2000®, Kemester 2000®, and Kemester 6000SE®, available from Crompton Corp.; Lamecreme DGE 18®, available from Cognis Corporation; Lexemul 515®, Lexemul 561®, Lexemul AR®, Lexemul AS®, Lexemul GDL®, and Lexemul T®, available from Inolex Chemical Co.; Lipomulse 165®, available from Lipo Chemicals, Inc.; Lumulse GML K®, Lumulse GMO K®, Lumulse GMR K®, and Lumulse GMT K®, available from Lambent Technologies Corp.; Magrabar GMC®, Magrabar GMO-CK®, Magrabar MDG-5050®, Magrabar PGO-315®, and Magrabar PGO-1010®, available from Magrabar Chemical Corp.; Mazol 300K®, Mazol GMO-K®, Mazol GMS-K®, and Mazol PGO31-K®, available from BASF Corp.; Miglyol 812®, available from Sasol North America Inc.; Norfox 165C®, available from Norman, Fox & Co.; Schercemol GMIS®, available from Noveon®, Inc.; Tegin®, Tegin 4100 Pellets®, Tegin M Pellets®, Tegin OV®, Teginacid H®, and Tego Cosmo P813®, available from Goldschmidt Chemical Corp.; Wickenol 535®, available from Alzo International, Inc.; Witconol 14®, available from Akzo Nobel Surface Chemistry LLC; Witconol 14®, Witconol 14F®, Witconol 18L®, Witconol GOT®, Witconol MST®, and Witconol RHT®, available from Crompton Corp.; Alkamuls 400-DO®; Dur-Em 114®; Dur-Em 117®; Dur-Em 204®; Dur-Em 207®; Dur-Em 207E®; Glicepol 160®; Glicepol 560®; Glicepol GMS 20®; Polyaldo 10-2-P®; Polyaldo DGDO®; Polyaldo HGDS®; Polyaldo TGMS®; Surfonic E400-MO®; and Tegin®;

Class M: Glycol Esters,

These include but are not limited to those selected from the list M which is defined as follows: List M:

Alkamuls 600 DO®, and Alkamuls SEG®, available from Rhodia, Inc.; Atlas EM-2®, available from Atlas Refinery Inc.; Cerasynt IP®, Cerasynt M®, Cerasynt MN®, and Cerasynt PA®, available from International Specialty Products/IS; Chemsperse EGDS®, and Chemsperse EGMS®, available from Chemron Corp.; Colonial Monolaurin®, available from Colonial Chemical Co.; DeMuls SGE-95®, available from DeForest Enterprises, Inc.; Eccoterge 200®, available from Eastern Color & Chemical Co.; Emerest 2380®, available from Cognis Corporation; Ethox 2610®, Ethox DO-9®, Ethox DO-14®, and Ethox SO-9®, available from Ethox Chemicals, LLC; Fizul MD-318®, available from Finetex Inc.; Genapol EGDS-VHP®, Genapol TS Powder®, and Hostacerin WO®, available from Clariant Corporation; Inversol 140®, available from Keil Chemical; Kemester 104®, Kemester 205®, Kemester 226®, Kemester 5221SE®, and Kemester EGDS®, available from Crompton Corp.; Lexemul EGDS®, Lexemul EGMS®, and Lexemul P®, available from Inolex Chemical Co.; Lipo DGLS®, Self-Emulsifying®, Lipo EGDS®, Lipo PGMS®, Liposorb S-4®, and Liposorb TO-20®, available from Lipo Chemicals, Inc.; Lumulse PGO®, available from Lambent Technologies Corp.; Mackester EGDS®, Mackester EGMS®, Mackester GSTP®, and Mackester Series®, available from The McIntyre Group; Magrabar PDG-50®, available from Magrabar Chemical Corp.; Mapeg 6000 DS®, available from BASF Corp.; Marlowet 4702®, available from Sasol North America Inc.; Monalube 305®, Monalube 310®, Monalube 315®, Monalube 320®, Monalube 325®, and Monalube 330®, available from Uniqema; Naturechem PGHS®, available from CasChem®, Inc.; Polycastorol PLO-840®, available from Magrabar Chemical Corp.; Polytex 10M®, available from Lipo Chemicals, Inc.; Ritasynt IP®, available from RITA Corp.; Ross Chem PEG 600 DT®, available from Lubrizol Foam Control Additives; Schercemol PGMS®, available from Noveon®, Inc.; Sponto H-44C®, available from Crompton Corp.; Tegin G®, available from Goldschmidt Chemical Corp.; Witbreak DGE-182®, available from Akzo Nobel Surface Chemistry LLC; Witbreak DGE-182®, available from Crompton Corp.; Witbreak DRA-21®, available from Akzo Nobel Surface Chemistry LLC; Witbreak DRA-21®, available from Crompton Corp.; Witbreak DRA-50®, available from Akzo Nobel Surface Chemistry LLC; Witbreak DRA-50®, available from Crompton Corp.; Witconol F26-46®, available from Crompton Corp.; Witconol H-32®, available from Akzo Nobel Surface Chemistry LLC; Witconol H-33®, available from Akzo Nobel Surface Chemistry LLC; Witconol H-35A®, available from Crompton Corp.; Witconol RHP®, available from Crompton Corp.; Ethox DO-14®; Ethox DO-9®; Pegosperse 100-L®; Pegosperse 100-O®; Pegosperse 100-S®; Pegosperse 1500-MS®; Pegosperse 1750-MS®; Pegosperse 200 DL®; Pegosperse 200-ML®; Pegosperse 400-DL®; Pegosperse 400-DO®; Pegosperse 400-DS®; Pegosperse 400-ML®; Pegosperse 400-MO®; Pegosperse 400-MOT®; Pegosperse 400-MS®; Pegosperse 50-DS®; Pegosperse 50-MS®; Pegosperse 600-ML®; Pegosperse 600-MS®; Protegin V®; Protegin W®; Protegin WX®; and Protegin XV®;

Class N: Lanolin-Based Derivatives

These include but are not limited to those selected from the list N which is defined as follows:

List N:
Amerchol CAB®, Amerchol L-101®, Amerlate LFA-LO®, and Amerlate P®, available from Amerchol Corp.; Barre Common Degras®, available from RITA Corp.; Cholesterol NF®, Crodalan AWS®, and Crodalan LA®, available from Croda Inc.; Emery 1650®, available from Cognis Canada Corp.; Emery 1650®, available from Cognis Corporation; Emery 1740®, available from Cognis Canada Corp.; Emery 1740®, available from Cognis Corporation; Forlan 500®, Forlan L®, Laneto 50®, Laneto 100®, and Laneto AWS®, available from RITA Corp.; Lanfrax 1776®, available from Cognis Canada Corp.; Lanfrax 1776®, available from Cognis Corporation; Lanogel 21®, available from Amerchol Corp.; Lipolan®, and Lipolan 31®, available from Lipo Chemicals, Inc.; OHlan®, available from Amerchol Corp.; Polychol 5®, and Polychol 15®, available from Croda Inc.; Ritacetyl®, Ritachol®, Ritahydrox®, Ritalafa®, Ritalan®, Ritalan AWS®, Ritalan C®, Ritawax®, Ritawax AEO®, and Ritawax ALA®, available from RITA Corp.; Solan/Solan 50/Super Solan®, and Super Hartolan/Hartolan®, available from Croda Inc.; and Supersat AWS-4®, and Supersat AWS-24®, available from RITA Corp.;

Class O: Lecithin and Lecithin Derivatives

These include but are not limited to those selected from the list O which is defined as follows: List O:

Alcolec®, available from American Lecithin Co.; Lecithin®, available from Archer Daniels Midland Company; and Lexin K®, and Natipide®, available from American Lecithin Co.;

Class P: Lignin and Lignin Derivatives

These include but are not limited to those selected from the list P which is defined as follows: List P:

Diwatex XP 9®, and Dynasperse LCD®, available from Borregaard Lignotech USA Inc.;

Indulin SAL®, Indulin W-1®, and Indulin W-5®, available from MeadWestvaco Corp.;

Lignosol FTA®, Lignosol SFX-65®, Marasperse 52 CP®, Marasperse AG®, Marasperse CBOS-4®, and Ufoxane 2®, available from Borregaard Lignotech USA Inc.;

Class Q: Methyl Esters

These include fatty acid methyl esters as described above, including but not limited to those selected from the list Q which is defined as follows:

List Q,
E.B. Cleaner AK®, available from Eastern Color & Chemical Co.; and Oleocal ME-70®, Oleocal ME-92®, Oleocal ME-112®, and Oleocal ME-130®, available from Lambent Technologies Corp.;

Class R: Monoglycerides and Derivatives

These include but are not limited to those selected from the list R which is defined as follows:

List R:
Dynacet 211®, available from Sasol North America Inc.; Hetsorb S-20®, available from Global-Seven, Inc.; Imwitor 191®, Imwitor 370®, Imwitor 375®, Imwitor 900®, Imwitor 945®, and Imwitor 2020®, available from Sasol North America Inc.; Kemester 5500®, and Kemester 6000®, available from Crompton Corp.; Magrabar GMC®, Magrabar GMO-CK®, Magrabar GPC-10®, and Magrabar MDG-5050®, available from Magrabar Chemical Corp.; Monalube 335®, available from Uniqema; Monoglycerides Glyceryl Monostearate Archer Daniels Midland Company; Rita GMS®, and Ritamulse SCG®, available from RITA Corp.; Softigen 701®, available from Sasol North America Inc.; and Tally 100 Plus®, available from Loders Croklaan U.S.A.;

Class S: Polyethylene Glycols i.e. $HO(CH_2CH_2O)_nH$, including but not limited to those selected from the list S which is defined as follows:

List S:

Polyethylene glycol 200 (mol wt range about 190-210); Polyethylene glycol 400 (mol wt range about 380-420); Polyethylene glycol 600 (mol wt range about 570-630); Polyethylene glycol 1500 (mol wt range about 1300-1600); Polyethylene glycol 4000 (mol wt range about 3000-3700); Polyethylene glycol 6000 (mol wt range about 7000-9000); Emulgade PL 68/50®, available from Cognis Corporation; Lumulse PEG®, available from Lambent Technologies Corp.; Rhodasurf PEG-400®, and Rhodasurf PEG-600®, available from Rhodia, Inc.; and Witconol PEG-400®, available from Akzo Nobel Surface Chemistry LLC;

Class T: Polymeric Surfactants

These include but are not limited to those selected from the list T which is defined as follows: List T:

Acritamer PNC-EG®, available from RITA Corp.; Ag-Rho DEP-775®, available from Rhodia, Inc.; APG 325N Glycoside®, available from Cognis Corporation; Aristoflex AVC®, and Aristoflex HMB®, available from Clariant Corporation; Burco NPS-225®, and Burco NPS-816®, available from Burlington Chemical Co.®, Inc.; Chemccinate 5603®, available from Chemron Corp.; Cosmedia Guar C-261N®, available from Cognis Corporation; Gantrez S-95®, available from International Specialty Products/IS; Glucopon 220 UP®, Glucopon 225 DK®, Glucopon 425 N®, Glucopon 600 UP®, and Glucopon 625 UP®, available from Cognis Corporation; Pemulen 1621®, Pemulen 1622®, Pemulen TR-1®, and Pemulen TR-2®, available from Noveon®, Inc.; Plantacare 818®, Plantapon LGC Sorb®, Plantaren 1200N®, and Plantaren 2000N®, available from Cognis Corporation; Viscolam AT 64®, Viscolam AT 64P®, Viscolam AT 100®, Viscolam MAC 7®, and Viscolam SMC 20®, available from RITA Corp.; Witbreak RTC-323®, available from Crompton Corp.; and WSI 3700®, available from Jacam Chemicals, L.L.C.;

Class U: Propoxylated & Ethoxylated Fatty Acids, Alcohols, or Alkyl Phenols

These include but are not limited to those selected from the list U which is defined as follows: List U:

Antarox AA-60®, and Antarox LF-224®, available from Rhodia, Inc.; Burcomul DFE-45®, and Burcoterge LFE-1000®, available from Burlington Chemical Co.®, Inc.; Chemal LF-25B®, and Chemal LF-40B®, available from Chemax Performance Solutions; Dehypon LS-36®, available from Cognis Canada Corp.; Dehypon LS-36®, available from Cognis Corporation; Dehypon LS-54®, available from Cognis Canada Corp.; Dehypon LS-54®, available from Cognis Corporation; Delonic 100 VLF®, and Delonic LF-60 MOD®, available from DeForest Enterprises, Inc.; Epiderm B®, available from Huntsman LLC; Ethylan 1206®, Ethylan NS-500K®, and Ethylan NS-500LQ®, available from Akzo Nobel Surface Chemistry LLC; Genapol 1392®, Genapol 2317®, Genapol 26EP710®, Genapol EP 1022®, Genapol EP 1024®, Genapol EP 6068®, and Genapol NP915®, available from Clariant Corporation; Kieralon MFB®, available from BASF Corp.; Lumisolve CSA-80 V®, available from Lambent Technologies Corp.; Marlowet 5001®, Marlox FK 64®, Marlox MO 124®, and Marlox S 58®, available from Sasol North America Inc.; Nonatell 1003®, Nonatell 1038®, Nonatell 1052®, Nonatell 1061®, Nonatell 1075®, Nonatell 1088®, Nonatell 1123®, Nonatell 1153®, Nonatell 1161®, Nonatell 1172®, and Nonatell 1181®, available from Tomah Products®, Inc.; Norfox 36®, available from Norman, Fox & Co.; Procetyl AWS®, available from Croda Inc.; Sandoxylate SX 412®Liquid, and Sandoxylate SX 418®, available from Clariant Corporation; Surfonic JL-80X®, Surfonic JL-80X-B1®, Surfonic L4-29X®, and Surfonic LF®, available from Huntsman LLC; T-Det A826®, and T-Det LF-416®, available from Harcros Chemicals Inc.; Tergitol Min-Foam 1X®, Tergitol Min-Foam 2X®, Triton CF-21®, Triton CF-76®, and Triton XL-80N®, available from Dow Chemical Company; Witconol NS-98®, Witconol NS-108LQ®, Witconol NS-145®, and Witconol NS-179®, available from Akzo Nobel Surface Chemistry LLC; Chemal LFL-17®; Chemal LFL-19®; Chemal LFL-28 C®; Chemal LFL-47®; Delonic LF-EP-15®; Delonic LF-EP-18®; Delonic LF-EP-20®; Delonic LF-EP-25®; Delonic LF-EP-30®; Delonic LF-EP-35®; Delonic LF-EP-40®; Delonic LF-EP-61®; Soprophor 796/P®;

Class V: Protein-Based Surfactants

These include but are not limited to those selected from the list V which is defined as follows: List V:

AminoFoam W®, available from Croda Inc.; Amiter LGOD-2®, Amiter LGS-2®, and Amiter LGS-5®, available from Ajinomoto USA, Inc.; Lamepon S®, available from Cognis Canada Corp.; Lamepon S®, available from Cognis Corporation; Maypon 4C®, available from Inolex Chemical Co.; May-Tein C®, May-Tein CT®, May-Tein KTS®, and May-Tein SY®, available from Maybrook, Inc.; Plantapon S®, available from Cognis Corporation; Proteol APL®, and Proteol OAT®, available from Seppic Inc.; Pyroter CPI-40®, and Pyroter GPI-25®, available from Ajinomoto USA, Inc.; Supro-Tein S®, and Supro-Tein V®, available from Maybrook, Inc.;

Class W: Sarcosine Derivatives

These include but are not limited to those selected from the list W which is defined as follows:

List W:

Crodasinic LS-30®, available from Croda Inc.; and Vanseal CS®, Vanseal LS®, Vanseal MS®, Vanseal NACS-30®, Vanseal NALS-95®, and Vanseal OS®, available from R. T. Vanderbilt Co. Inc.;

Class X: Silicone-Based Surfactants

These include but are not limited to those selected from the list X which is defined as follows: List X:

Abil-B-9950®, Abil Care 85®, Abil EM 90®, Abil EM 97®, and Abil WE-09®, available from Goldschmidt Chemical Corp.; Dow Corning 1248 Fluid®, Dow Corning 3225C®Formulation Aid, Dow Corning 5200®Formulation Aid, and Dow Corning Q4-3667®Fluid, available from Dow Corning Corp.; Monasil PCA®, Monasil PDM®, and Monasil PLN®, available from Uniqema; Polyderm PPI-SI-WS®, available from Alzo International, Inc.; Troysol 380 W®, and Troysol S366®, available from Troy Corporation; Abil-B-88183®; Abil-B-8832®; Abil-B-8843®; Abil-B-8851®; Abil-B-8852®; Abil-B-8863®; Dow Corning 190 Surfactant®; Dow Corning 193 Surfactant®; Dow Corning 5103 Surfactant®; Dow Corning FF400 Fluid®; Silwet L-7001®; Silwet L-7002®; Silwet L-7087®; Silwet L-720®; Silwet L-7200®; Silwet L-7210®; Silwet L-722®; Silwet L-7220®; Silwet L-7230®; Silwet L-7500®; Silwet L-7600®; Silwet L-7602®; Silwet L-7604®; Silwet L-7605®; Silwet L-7607®; Silwet L-7608®; Silwet L-7622®; Silwet L-7657®; and Silwet L-77®;

Class Y: Sorbitan Derivatives

These are ethoxylated sorbates having a fatty acid capping one or more of the ethoxylated chains. For example, polysorbate 80 has an oleate cap as shown in the structure below.

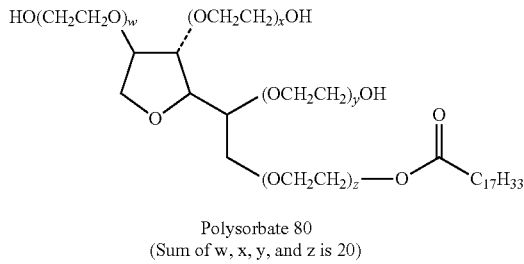

Polysorbate 80
(Sum of w, x, y, and z is 20)

These compounds are named as POE (w+x+y+z) sorbitan mono (or di- or tri-) fatty acid.

For example, Polysorbate 80 is POE (2O) sorbitan monooleate.

Thus, the number in parenthesis is the total number of ethylene oxide units on the molecule, and the ending is the number of acid caps and the capping acid.

These include but are not limited to those selected from the list Y which is defined as follows:

List Y:
Sorbitan derivatives wherein the total number of ethylene oxide units is from 3 to 30;
Sorbitan derivatives wherein the total number of ethylene oxide units is 4, 5, or 20;
Sorbitan derivatives wherein the capping acid is laurate, palmitate, stearate, or oleate;
The sorbitan derivative may be a POE sorbitan monolaurate;
a POE sorbitan dilaurate;
a POE sorbitan trilaurate;
a POE sorbitan monopalmitate;
a POE sorbitan dipalmitate;
a POE sorbitan tripalmitate;
a POE sorbitan monostearate;
a POE sorbitan distearate;
a POE sorbitan tristearate;
a POE sorbitan monooleate;
a POE sorbitan dioleate; and/or
a POE sorbitan trioleate;
POE (20) sorbitan monolaurate; POE (4) sorbitan monolaurate; POE (20) sorbitan monopalmitate; POE (20) monostearate; POE (20) sorbitan monostearate; POE (4) sorbitan monostearate; POE (20) sorbitan tristearate; POE (20) sorbitan monooleate; POE (20) sorbitan 15 monooleate; POE (5) sorbitan 10 monooleate; POE (20) sorbitan trioleate; specific examples include Alkamuls SML®, Alkamuls SMO®, and Alkamuls STO®, available from Rhodia, Inc.; Arlacel 20®, Arlacel 40®, Arlacel 60®, Arlacel 80®, and Arlacel C®, available from Uniqema; Armul 21®, available from Crompton Corp.; Atlox 80®, Atlox 847®, Atlox 1045A®, available from Uniqema; Canarcel 20®, Canarcel 60®, Canarcel 80®, Canarcel TW 20®, Canarcel TW 60®, and Canarcel TW 80®, available from Canamex Quimicos S.A de C.v; Coladet BSB-P®, available from Colonial Chemical Co.; Customulse O-20®, available from Custom Ingredients, Inc.; Dehymuls E®, available from Cognis Canada Corp.; DeSotan SMO®, DeSotan SMO-20®, DeSotan SMT®, and DeSotan SMT-20®, available from Crompton Corp.; Durfax 60®, Durfax 65®, Durfax 80®, Durtan 60®, and Durtan 65®, available from Loders Croklaan U.S.A.; Liposorb L®, Liposorb L-10®, Liposorb L-20®, Liposorb O®, Liposorb O-20®, Liposorb P®, Liposorb P-20®, Liposorb S®, Liposorb S-20®, Liposorb SQO®, Liposorb TO®, Liposorb TS®, and Liposorb TS-20®, available from Lipo Chemicals, Inc.; Lumisorb PS®, Lumisorb SMO (T)®, Lumisorb SMS K®, Lumisorb SSO®, Lumisorb STS K®, and Lumisorb STT®, available from Lambent Technologies Corp.; Magrabar SMO®, Magrabar SMO-VEG®, Magrabar SMT®, and Magrabar STO®, available from Magrabar Chemical Corp.; Miracare BC-27®, available from Rhodia, Inc.; Ritabate 20®, Ritabate 40®, Ritabate 60®, and Ritabate 80®, available from RITA Corp.; T-Maz®, available from BASF Corp.; Tego SML®, Tego SML 20®, Tego SMO 80 V®, Tego SMO V®, Tego SMS®, and Tego STO V®, available from Goldschmidt Chemical Corp.; Tween 21®, Tween 40®, Tween 60®, Tween 60 K®, Tween 61®, Tween 65®, Tween 80®, Tween 80 K®, Tween 81®, and Tween 85®, available from Uniqema; Alkamuls PSML-20®; Alkamuls PSMO-20®; Alkamuls PSTO-20®; Cremophor PS150®; Cremophor PS20®; Cremophor PS28®; Cremophor PS60®; Cremophor PS80®; Crill 3®; Crill 4®; Crill 6®; Crillet 3®; Crillet 4®; Crillet 6®; Glycomul L®; Glycomul O®; Glycomul S®; Glycomul TO®; Glycomul TS®; Hetsorb L-20®; Hetsorb L-4®; Hetsorb L-80-72%®; Hetsorb 0-20®; Hetsorb 0-5®; Hetsorb TO-20®; Lumisorb PSML-20 K®; Lumisorb PSML-20 NF®; Lumisorb PSMO-20 K®; Lumisorb PSMO-5 K®; Lumisorb PSMS-20 K®; Lumisorb PSTS-20 K®; Lumisorb PSTT-20 K®; Sorbax PML-20®; Sorbax PMO-20®; Sorbax PMO-5®; Sorbax PMP-20®; Sorbax PMS-20®; Sorbax PTO-20®; Sorbax PTS-20®; Sorbax SML®; Sorbax SMO®; Sorbax SMP®; Sorbax SMS®; Sorbax STO®; Sorbax STS®; Span 20®; Span 40®; Span 60®; Span 60K®; Span 65®; Span 80®; Span 85®; T-Maz 20®; T-Maz 28®; T-Maz 60K®; T-Maz 65K®; T-Maz 80®; T-Maz 80K®; T-Maz 81®; T-Maz 85®; and T-Maz 90®;

Class Z: Sucrose and Glucose Esters and Derivatives

These include but are not limited to those selected from the list Z which is defined as follows:

List Z:
DeSulf GOS-P-60WCG®, available from DeForest Enterprises, Inc.; Glucam E-20 Distearate®, Glucamate DOE-120®, Glucamate SSE-20®, Glucate DO®, and Glucate SS®, available from Amerchol Corp.; Glucopon 425 UP®, available from Cognis Corporation; Isolan IS®, available from Goldschmidt Chemical Corp.; Mazon 40®, available from BASF Corp.; Montanov 82®, Montanov 202®, and Montanov S®, available from Seppic Inc.; Rheozan®, available from Rhodia, Inc.; Simulsol AS 48®, Simulsol SL 4®, Simulsol SL 10®, Simulsol SL 11W®, and Simulsol SL 55®, available from Seppic Inc.; Suga Nate 100 and 160®, available from Colonial Chemical Co.; Tego Care 450®, Tego Care CG 90®, Tego Care PS®, Tegosoft PSE 141 G®, and Tegotens G 826®, available from Goldschmidt Chemical Corp.; Triton BG-10 (70%)®, and Triton CG-110 (60%)®, available from Dow Chemical Company; Wickenol 545®, available from Alzo International, Inc; Tego Care 150®; Tego Care 215®; and Triton CG-110 (60%)®.

Class Z': Other

The surfactant may also be selected from the list Z' which is defined as follows:

List Z':

A sorbitan ester; Polysorbate 20, Polysorbate 40, Polysorbate 60, Polysorbate 80, a stearate, glyceryl stearate, isopropyl stearate, polyoxyl stearate, propylene glycol stearate, sucrose stearate, polyethylene glycol, polyethylene oxide, polypropylene oxide, a polyethylene oxide-polypropylene oxide copolymer, an alcohol ethoxylate, an alkylphenol ethoxylate, an alkyl glycoside, alkyl polyglycoside, a fatty alcohol, a cellulose derivative, hydroxypropylmethyl cellulose, carboxymethyl cellulose, a polyacrylic acid, a carbomer, a phospholipid, phosphatidyl choline, a phosphatidyl serine and Pluronic from BASF The Composition Where the composition comprises cyclosporin A and an oil having a specific gravity from 0.95 to 1.07 the surfactant may be of Class A, B, C, D, E, F, G, H, I, J, K, L, M, N, O, P, Q, R, S, T, U, V, W, X, Y, Z or Z' above. The surfactant may be any of those set out in Lists A, B, C, D, E, F, G, H, I, J, K, L, M, N, O, P, Q, R, S, T, U, V, W, X, Y, Z or Z' above.

Where the composition comprises cyclosporin A and Anise oil the surfactant may be of Class A, B, C, D, E, F, G, H, I, J, K, L, M, N, O, P, Q, R, S, T, U, V, W, X, Y, Z or Z' above. The surfactant may be any of those set out in Lists A, B, C, D, E, F, G, H, I, J, K, L, M, N, O, P, Q, R, S, T, U, V, W, X, Y, Z or Z' above. Where the composition comprises cyclosporin A and Castor oil the surfactant may be of Class A, B, C, D, E, F, G, H, I, J, K, L, M, N, O, P, Q, R, S, T, U, V, W, X, Y, Z or Z' above. The surfactant may be any of those set out in Lists A, B, C, D, E, F, G, H, I, J, K, L, M, N, O, P, Q, R, S, T, U, V, W, X, Y, Z or Z' above. Where the composition comprises cyclosporin A and Clove oil the surfactant may be of Class A, B, C, D, E, F, G, H, I, J, K, L, M, N, O, P, Q, R, S, T, U, V, W, X, Y, Z or Z' above. The surfactant may be any of those set out in Lists A, B, C, D, E, F, G, H, I, J, K, L, M, N, O, P, Q, R, S, T, U, V, W, X, Y, Z or Z' above. Where the composition comprises cyclosporin A and Cassia oil the surfactant may be of Class A, B, C, D, E, F, G, H, I, J, K, L, M, N, O, P, Q, R, S, T, U, V, W, X, Y, Z or Z' above. The surfactant may be any of those set out in Lists A, B, C, D, E, F, G, H, I, J, K, L, M, N, O, P, Q, R, S, T, U, V, W, X, Y, Z or Z' above. Where the composition comprises cyclosporin A and Cinnamon oil the surfactant may be of Class A, B, C, D, E, F, G, H, I, J, K, L, M, N, O, P, Q, R, S, T, U, V, W, X, Y, Z or Z' above. The surfactant may be any of those set out in Lists A, B, C, D, E, F, G, H, I, J, K, L, M, N, O, P, Q, R, S, T, U, V, W, X, Y, Z or Z' above. Where the composition comprises cyclosporin A and an oil having a specific gravity from 0.90 to 0.95 the surfactant may be of Class A, B, C, D, E, F, G, H, I, J, K, L, M, N, O, P, Q, R, S, T, U, V, W, X, Y, Z or Z' above. The surfactant may be any of those set out in Lists A, B, C, D, E, F, G, H, I, J, K, L, M, N, O, P, Q, R, S, T, U, V, W, X, Y, Z or Z' above. Where the composition comprises cyclosporin A and Almond oil the surfactant may be of Class A, B, C, D, E, F, G, H, I, J, K, L, M, N, O, P, Q, R, S, T, U, V, W, X, Y, Z or Z' above. The surfactant may be any of those set out in Lists A, B, C, D, E, F, G, H, I, J, K, L, M, N, O, P, Q, R, S, T, U, V, W, X, Y, Z or Z' above. Where the composition comprises cyclosporin A and Corn oil the surfactant may be of Class A, B, C, D, E, F, G, H, I, J, K, L, M, N, O, P, Q, R, S, T, U, V, W, X, Y, Z or Z' above. The surfactant may be any of those set out in Lists A, B, C, D, E, F, G, H, I, J, K, L, M, N, O, P, Q, R, S, T, U, V, W, X, Y, Z or Z' above. Where the composition comprises cyclosporin A and Arachis oil the surfactant may be of Class A, B, C, D, E, F, G, H, I, J, K, L, M, N, O, P, Q, R, S, T, U, V, W, X, Y, Z or Z' above. The surfactant may be any of those set out in Lists A, B, C, D, E, F, G, H, I, J, K, L, M, N, O, P, Q, R, S, T, U, V, W, X, Y, Z or Z' above.

Where the composition comprises cyclosporin A and Cottonseed oil the surfactant may be of Class A, B, C, D, E, F, G, H, I, J, K, L, M, N, O, P, Q, R, S, T, U, V, W, X, Y, Z or Z' above. The surfactant may be any of those set out in Lists A, B, C, D, E, F, G, H, I, J, K, L, M, N, O, P, Q, R, S, T, U, V, W, X, Y, Z or Z' above. Where the composition comprises cyclosporin A and Safflower oil the surfactant may be of Class A, B, C, D, E, F, G, H, I, J, K, L, M, N, O, P, Q, R, S, T, U, V, W, X, Y, Z or Z' above. The surfactant may be any of those set out in Lists A, B, C, D, E, F, G, H, I, J, K, L, M, N, O, P, Q, R, S, T, U, V, W, X, Y, Z or Z' above. Where the composition comprises cyclosporin A and Maize oil the surfactant may be of Class A, B, C, D, E, F, G, H, I, J, K, L, M, N, O, P, Q, R, S, T, U, V, W, X, Y, Z or Z' above. The surfactant may be any of those set out in Lists A, B, C, D, E, F, G, H, I, J, K, L, M, N, O, P, Q, R, S, T, U, V, W, X, Y, Z or Z' above. Where the composition comprises cyclosporin A and Linseed oil the surfactant may be of Class A, B, C, D, E, F, G, H, I, J, K, L, M, N, O, P, Q, R, S, T, U, V, W, X, Y, Z or Z' above. The surfactant may be any of those set out in Lists A, B, C, D, E, F, G, H, I, J, K, L, M, N, O, P, Q, R, S, T, U, V, W, X, Y, Z or Z' above. Where the composition comprises cyclosporin A and Rapeseed oil the surfactant may be of Class A, B, C, D, E, F, G, H, I, J, K, L, M, N, O, P, Q, R, S, T, U, V, W, X, Y, Z or Z' above. The surfactant may be any of those set out in Lists A, B, C, D, E, F, G, H, I, J, K, L, M, N, O, P, Q, R, S, T, U, V, W, X, Y, Z or Z' above. Where the composition comprises cyclosporin A and Soybean oil the surfactant may be of Class A, B, C, D, E, F, G, H, I, J, K, L, M, N, O, P, Q, R, S, T, U, V, W, X, Y, Z or Z' above. The surfactant may be any of those set out in Lists A, B, C, D, E, F, G, H, I, J, K, L, M, N, O, P, Q, R, S, T, U, V, W, X, Y, Z or Z' above. Where the composition comprises cyclosporin A and Olive oil the surfactant may be of Class A, B, C, D, E, F, G, H, I, J, K, L, M, N, O, P, Q, R, S, T, U, V, W, X, Y, Z or Z' above. The surfactant may be any of those set out in Lists A, B, C, D, E, F, G, H, I, J, K, L, M, N, O, P, Q, R, S, T, U, V, W, X, Y, Z or Z' above. Where the composition comprises cyclosporin A and Caraway oil the surfactant may be of Class A, B, C, D, E, F, G, H, I, J, K, L, M, N, O, P, Q, R, S, T, U, V, W, X, Y, Z or Z' above. The surfactant may be any of those set out in Lists A, B, C, D, E, F, G, H, I, J, K, L, M, N, O, P, Q, R, S, T, U, V, W, X, Y, Z or Z' above. Where the composition comprises cyclosporin A and Rosemary oil the surfactant may be of Class A, B, C, D, E, F, G, H, I, J, K, L, M, N, O, P, Q, R, S, T, U, V, W, X, Y, Z or Z' above. The surfactant may be any of those set out in Lists A, B, C, D, E, F, G, H, I, J, K, L, M, N, O, P, Q, R, S, T, U, V, W, X, Y, Z or Z' above. Where the composition comprises cyclosporin A and Peanut oil the surfactant may be of Class A, B, C, D, E, F, G, H, I, J, K, L, M, N, O, P, Q, R, S, T, U, V, W, X, Y, Z or Z' above. The surfactant may be any of those set out in Lists A, B, C, D, E, F, G, H, I, J, K, L, M, N, O, P, Q, R, S, T, U, V, W, X, Y, Z or Z' above. Where the composition comprises cyclosporin A and Peppermint oil the surfactant may be of Class A, B, C, D, E, F, G, H, I, J, K, L, M, N, O, P, Q, R, S, T, U, V, W, X, Y, Z or Z' above. The surfactant may be any of those set out in Lists A, B, C, D, E, F, G, H, I, J, K, L, M, N, O, P, Q, R, S, T, U, V, W, X, Y, Z or Z' above. Where the composition comprises cyclosporin A and Sunflower oil the surfactant may be of Class A, B, C, D, E, F, G, H, I, J, K, L, M, N, O, P, Q, R, S, T, U, V, W, X, Y, Z or Z' above. The surfactant may be any of those set out in Lists A, B, C, D, E, F, G, H, I, J, K, L, M, N, O, P, Q, R, S, T, U, V, W, X, Y, Z or Z' above.

Where the composition comprises cyclosporin A and Eucalyptus oil the surfactant may be of Class A, B, C, D, E, F, G, H, I, J, K, L, M, N, O, P, Q, R, S, T, U, V, W, X, Y, Z or Z' above. The surfactant may be any of those set out in Lists A, B, C, D, E, F, G, H, I, J, K, L, M, N, O, P, Q, R, S, T, U, V, W, X, Y, Z or Z' above. Where the composition comprises cyclosporin A and Sesame oil the surfactant may be of Class A, B, C, D, E, F, G, H, I, J, K, L, M, N, O, P, Q, R, S, T, U, V, W, X, Y, Z or Z' above. The surfactant may be any of those set out in Lists A, B, C, D, E, F, G, H, I, J, K, L, M, N, O, P, Q, R, S, T, U, V, W, X, Y, Z or Z' above. Where the composition comprises cyclosporin A and an oil having a specific gravity below 0.9, the surfactant may be of Class A, B, C, D, E, F, G, H, I, J, K, L, M, N, O, P, Q, R, S, T, U, V, W, X, Y, Z or Z' above. The surfactant may be any of those set out in Lists A, B, C, D, E, F, G, H, I, J, K, L, M, N, O, P, Q, R, S, T, U, V, W, X, Y, Z or Z' above. Where the composition comprises cyclosporin A and Mineral oil the surfactant may be of Class A, B, C, D, E, F, G, H, I, J, K, L, M, N, O, P, Q, R, S, T, U, V, W, X, Y, Z or Z' above. The surfactant may be any of those set out in Lists A, B, C, D, E, F, G, H, I, J, K, L, M, N, O, P, Q, R, S, T, U, V, W, X, Y, Z or Z' above.

Where the composition comprises cyclosporin A and Coriander oil the surfactant may be of Class A, B, C, D, E, F, G, H, I, J, K, L, M, N, O, P, Q, R, S, T, U, V, W, X, Y, Z or Z' above. The surfactant may be any of those set out in Lists A, B, C, D, E, F, G, H, I, J, K, L, M, N, O, P, Q, R, S, T, U, V, W, X, Y, Z or Z' above. Where the composition comprises cyclosporin A and Lavender oil the surfactant may be of Class A, B, C, D, E, F, G, H, I, J, K, L, M, N, O, P, Q, R, S, T, U, V, W, X, Y, Z or Z' above. The surfactant may be any of those set out in Lists A, B, C, D, E, F, G, H, I, J, K, L, M, N, O, P, Q, R, S, T, U, V, W, X, Y, Z or Z' above. Where the composition comprises cyclosporin A and Citronella oil the surfactant may be of Class A, B, C, D, E, F, G, H, I, J, K, L, M, N, O, P, Q, R, S, T, U, V, W, X, Y, Z or Z' above. The surfactant may be any of those set out in Lists A, B, C, D, E, F, G, H, I, J, K, L, M, N, O, P, Q, R, S, T, U, V, W, X, Y, Z or Z' above. Where the composition comprises cyclosporin A and Juniper oil the surfactant may be of Class A, B, C, D, E, F, G, H, I, J, K, L, M, N, O, P, Q, R, S, T, U, V, W, X, Y, Z or Z' above. The surfactant may be any of those set out in Lists A, B, C, D, E, F, G, H, I, J, K, L, M, N, O, P, Q, R, S, T, U, V, W, X, Y, Z or Z' above.

Where the composition comprises cyclosporin A and Lemon oil the surfactant may be of Class A, B, C, D, E, F, G, H, I, J, K, L, M, N, O, P, Q, R, S, T, U, V, W, X, Y, Z or Z' above. The surfactant may be any of those set out in Lists A, B, C, D, E, F, G, H, I, J, K, L, M, N, O, P, Q, R, S, T, U, V, W, X, Y, Z or Z' above. Where the composition comprises cyclosporin A and Orange oil the surfactant may be of Class A, B, C, D, E, F, G, H, I, J, K, L, M, N, O, P, Q, R, S, T, U, V, W, X, Y, Z or Z' above. The surfactant may be any of those set out in Lists A, B, C, D, E, F, G, H, I, J, K, L, M, N, O, P, Q, R, S, T, U, V, W, X, Y, Z or Z' above. Where the composition comprises cyclosporin A and Clary sage oil the surfactant may be of Class A, B, C, D, E, F, G, H, I, J, K, L, M, N, O, P, Q, R, S, T, U, V, W, X, Y, Z or Z' above. The surfactant may be any of those set out in Lists A, B, C, D, E, F, G, H, I, J, K, L, M, N, O, P, Q, R, S, T, U, V, W, X, Y, Z or Z' above. Where the composition comprises cyclosporin A and Nutmeg oil the surfactant may be of Class A, B, C, D, E, F, G, H, I, J, K, L, M, N, O, P, Q, R, S, T, U, V, W, X, Y, Z or Z' above. The surfactant may be any of those set out in Lists A, B, C, D, E, F, G, H, I, J, K, L, M, N, O, P, Q, R, S, T, U, V, W, X, Y, Z or Z' above.

Where the composition comprises cyclosporin A and Tea tree oil the surfactant may be of Class A, B, C, D, E, F, G, H, I, J, K, L, M, N, O, P, Q, R, S, T, U, V, W, X, Y, Z or Z' above. The surfactant may be any of those set out in Lists A, B, C, D, E, F, G, H, I, J, K, L, M, N, O, P, Q, R, S, T, U, V, W, X, Y, Z or Z' above.

A liquid or emulsion which is ophthalmically acceptable is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid or emulsion should either be packaged for single use, or contain a preservative to prevent contamination over multiple uses.

In accordance with the present invention, the emulsions can be further stabilized using a polyelectrolyte, or polyelectrolytes if more than one, from the family of cross-linked polyacrylates, such as carbomers and Pemulen®.

Pemulene® is a registered trademark of B.F. Goodrich for polymeric emulsifiers and commercially available from B.F. Goodrich Company, Specialty Polymers & Chemicals Division, Cleveland, Ohio. Pemulens are Acrylates/C10-30 Alkyl Acrylate Cross-Polymers. They are high molecular weight co-polymers of acrylic acid and a long chain alkyl methacrylate cross-linked with allyl ethers of pentaerythritol. They contain not less than 52.0 percent and not more than 62.0 percent of carboxylic acid groups. The viscosity of a neutralized 1.0 percent aqueous dispersion is between 9,500 and 26,500 centipoises.

In addition, the tonicity of the emulsions can be further adjusted using glycerine, mannitol, or sorbitol if desired. The pH of the emulsions can be adjusted in a conventional manner using sodium hydroxide to a near physiological pH level and while buffering agents are not required, suitable buffers may include phosphates, citrates, acetates and borates.

Examples of useful formulations are shown below (the reference to Brij®78 in the table is to a trademark to Polyoxyethylene (20) Stearyl Ether).

| Ingredients | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| Cyclosporine A | 0.1 | 0.1 | 0.05 | 0.02 | 0.05 | 0.03 | 0.01 | 0.08 | 0.03 | 0.1 | 0.04 | 0.05 | 0.08 | 0.02 | 0.05 |
| Castor oil | 1.00 | 1.2 | | | | | | 0.50 | 0.50 | | | | 0.50 | | |
| Clove oil | 0.70 | | | | 0.50 | 0.40 | 0.20 | | | | 0.50 | 0.80 | | | |
| *Cassia* oil | | 0.4 | 0.20 | 0.70 | | | | 0.55 | | 0.75 | | | | | |
| Cottonseed oil | | | 0.60 | | | | | | | | | | | | |
| Soybean oil | | | | | | | 0.30 | | | | | | | | |
| Lavender oil | | | | | 0.30 | | | | | | 0.90 | | | | 1.00 |
| Juniper oil | | | | | | 0.20 | | | | | | | | | |
| Corn oil | | | | 0.70 | | | | | | | | 0.40 | | | |
| Olive oil | | | | | | | | | 0.35 | | | | | 1.00 | |

-continued

| Ingredients | 1 | 2 | 3 | 4 | 5 | 6 | 7 | 8 | 9 | 10 | 11 | 12 | 13 | 14 | 15 |
|---|---|---|---|---|---|---|---|---|---|---|---|---|---|---|---|
| Mineral Oil | | | | | | | | | | | | | 0.80 | | |
| Polysorbate-80 | 1.00 | 0.80 | | 1.50 | | | 0.30 | | 0.30 | 0.30 | 0.10 | 0.30 | | | 0.60 |
| Diglycerol | 0.70 | | | | | | | 0.20 | | | | | 0.80 | | |
| Polyglycerol-3 | | | 1.00 | | | 0.10 | | | | | 0.80 | | | | |
| Simulsol OX 1005L | | 0.60 | | | | | | | | | | | | | |
| Chemonic 435 | | | | | | | | | | | | | | | |
| Marlowet 4530 | | | | | | | | | | | | | | | |
| Brij52 | | | 0.50 | | 0.70 | 0.60 | | | | | | | | | |
| Brij78 | | | | | | | | 1.20 | | | | | | 0.80 | |
| Bio Soft TD-630 | | | | | | | | | | 1.3 | | | | | |
| Canasol BJ 78 | | | | | 0.50 | | | | | | | | | | |
| Canasol BJ 52 | | | 0.30 | | | | | | | | 0.80 | | | | |
| Rhodasurf BEH 25 | | | | | | | | | | | | | | | |
| Desonic 9D | | | | | | | | | | | | 0.60 | | | 0.40 |
| Glycerin | 2.00 | 1.70 | 1.50 | 2.00 | 1.00 | 2.00 | 2.00 | 2.00 | 2.00 | 2.00 | 1.50 | 2.00 | 2.00 | 1.20 | 2.00 |
| CMC | 0.50 | | | | 0.50 | | | 0.50 | | | | | | 0.50 | |
| Pemulen TR-2 | | 0.05 | 0.03 | 0.05 | | | | | 0.02 | | | 0.02 | | | |
| Purified Water | QS | QS | QS | QS | QS | QS | QS | QS | QS | QS | QS | QS | QS | QS | QS |
| Sodium Hydroxide | pH adj | pH adj | pH adj | pH adj | pH adj | pH adj | pH adj | pH adj | pH adj | pH adj | pH adj | pH adj | pH adj | pH adj | pH adj |
| PH | 7.2 | 7.5 | 6.3 | 7.3 | 7.4 | 7.8 | 6.8 | 7.1 | 6.8 | 7 | 7.2 | 7.2 | 7.4 | 7.6 | 5.9 |

Another useful emulsion consists of the following: 0.1% cyclosporin A, 0.20% castor oil, 0.75% polyethylene oxide 40 stearate (Myrj 52®), 0.2% Polysorbate 80, 1.0% glycerin, 0.6% boric acid, 0.5% carboxymethylcellulose, 100 ppm stabilized oxychloro complex (Purite®), sufficient sodium hydroxide to adjust the pH, and the remainder water, wherein the pH is from 7.3 to 7.5.

Although there has been hereinabove described a particular pharmaceutical composition in the form of a nonirritating emulsion for the purpose of illustrating the manner in which the invention may be used to advantage, it should be appreciated that the invention is not limited thereto. Accordingly, any and all modifications, variations, or equivalent arrangements, which may occur to those skilled in the art, should be considered to be within the scope of the present invention as defined in the appended claims.

What is claimed is:

1. A method of treating dry eye disease comprising administering to an eye of a mammal in need of such treatment an ophthalmically acceptable emulsion comprising from about 0.001% to about 0.1% cyclosporin A, a combination of castor oil and olive oil, a surfactant, and carboxymethylcellulose, wherein the surfactant is selected from the group consisting of Polysorbate 80, Polysorbate 60, Polysorbate 40, Polysorbate 20, a stearate surfactant, glyceryl stearate, isopropyl stearate, polyoxyl stearate, propylene glycol stearate, sucrose stearate, polyethylene glycol, polyethylene oxide, polypropylene oxide, a polyethylene oxide-polypropylene oxide copolymer, an alcohol ethoxylate, an alkylphenol ethoxylate, an alkyl glycoside, an alkyl polyglycoside, a fatty alcohol, a cellulose derivative, hydroxypropylmethyl cellulose, carboxymethyl cellulose, a polyacrylic acid, a Carbomer, a phosphalipid, phosphatidyl chloline, and a phosphatidyl serine.

2. The method of claim 1, wherein the ophthalmically acceptable emulsion further comprises cassia oil.

3. The method of claim 1, wherein the ophthalmically acceptable emulsion further comprises Polyoxyethylene (20) Stearyl Ether.

* * * * *